(12) United States Patent
Archibald et al.

(10) Patent No.: US 7,887,838 B2
(45) Date of Patent: Feb. 15, 2011

(54) NON-GELATIN FILM AND METHOD AND APPARATUS FOR PRODUCING SAME

(75) Inventors: Don A. Archibald, Jamestown, NC (US); Qi Fang, Greensboro, NC (US); Linus G. Fonkwe, High Point, NC (US); Gregory L. Dietel, Brown Summit, NC (US); Charles S. Casault, Kernersville, NC (US)

(73) Assignee: Banner Pharmacaps, Inc., High Point, NC (US)

( * ) Notice: Subject to any disclaimer, the term of this patent is extended or adjusted under 35 U.S.C. 154(b) by 1633 days.

(21) Appl. No.: 10/610,306

(22) Filed: Jun. 30, 2003

(65) Prior Publication Data

US 2004/0052839 A1    Mar. 18, 2004

Related U.S. Application Data

(63) Continuation-in-part of application No. 10/051,201, filed on Jan. 18, 2002, now Pat. No. 6,949,256.

(51) Int. Cl.
*A61K 9/48* (2006.01)
*C08B 39/00* (2006.01)

(52) U.S. Cl. .................... 424/452; 424/2.14; 536/1.11; 536/124; 514/23; 514/54; 514/60

(58) Field of Classification Search ................ 424/452, 424/2.14; 536/1.11, 124; 514/23, 54, 60
See application file for complete search history.

(56) References Cited

U.S. PATENT DOCUMENTS

| | | | |
|---|---|---|---|
| 2,802,000 A | 8/1957 | Caldwell | 260/233.3 |
| 2,813,093 A | 11/1957 | Caldwell | 260/233.3 |
| 2,825,727 A | 3/1958 | Caldwell | 260/233.3 |
| 3,058,827 A | 10/1962 | Graham | 96/111 |
| 3,329,509 A | 7/1967 | Julius | 99/171 |
| 3,499,962 A | 3/1970 | Wurzburg et al. | 424/35 |
| 3,607,394 A | 9/1971 | Germino | 127/32 |
| 3,865,603 A | 2/1975 | Szymanski et al. | 106/130 |
| 3,956,173 A | 5/1976 | Towle | 252/316 |
| 3,962,482 A | 6/1976 | Comer et al. | 426/575 |
| 4,009,291 A | 2/1977 | Mitchell et al. | 426/548 |
| 4,026,986 A | 5/1977 | Christen et al. | 264/301 |
| 4,129,134 A | 12/1978 | Hind et al. | 131/2 |
| 4,231,803 A | 11/1980 | Bovier et al. | 106/213 |
| 4,276,320 A | 6/1981 | Moirano | 426/575 |
| 4,600,439 A | 7/1986 | Schneider et al. | 106/139 |
| 4,615,897 A | 10/1986 | Brown et al. | 426/576 |
| 4,632,848 A | 12/1986 | Gosset et al. | 427/154 |
| 4,760,129 A | 7/1988 | Haering et al. | 528/481 |
| 4,795,642 A | 1/1989 | Cohen et al. | 424/455 |
| 4,804,542 A | 2/1989 | Fischer et al. | 424/456 |
| 4,935,243 A | 6/1990 | Borkan et al. | 424/441 |
| 5,002,934 A | 3/1991 | Norton et al. | 514/54 |
| 5,089,307 A * | 2/1992 | Ninomiya et al. | 428/35.2 |
| 5,146,730 A | 9/1992 | Sadek et al. | 53/454 |
| 5,334,640 A | 8/1994 | Desai et al. | 524/56 |
| 5,342,626 A | 8/1994 | Winston, Jr. et al. | 424/461 |
| 5,393,054 A | 2/1995 | Rouffer | 273/58 |
| 5,451,673 A | 9/1995 | Fishman et al. | 536/123 |
| 5,459,983 A | 10/1995 | Sadek et al. | 53/560 |
| 5,484,598 A | 1/1996 | Schurig et al. | 424/401 |
| 5,550,178 A | 8/1996 | Desai et al. | 524/56 |
| 5,554,385 A | 9/1996 | Stroud | 424/456 |
| 5,620,757 A | 4/1997 | Ninomiya et al. | 428/34.8 |
| 5,656,294 A | 8/1997 | Friend et al. | 424/465 |

(Continued)

FOREIGN PATENT DOCUMENTS

CA        2243227        5/1999

(Continued)

OTHER PUBLICATIONS

Ionnis Arvanitoyannis, et al., "Edible films made from sodium caseinate, starches, sugars or glycerol. Part 1", *Carbohydrate Polymers*, 31:179-192 (1996).

Ioannis Arvanitoyannis, et al., "Biodegradable films made from low-density polyethylene (LDPE), rice starch and potato starch for food packaging applications: Part 1", *Carbohydrate Polymers*, 36:89-104 (1998).

Eleni Psomiadou, et al., "Edible films made from natural resources; microcrystalline cellulose (MCC), methylcellulose (MC) and corn starch and polyols—Part 2", *Carbohydrate Polymers*, 31:193-204 (1996).

Krochta, et al., "Edible and Biodegradable Polymer Films: Challenges and Opportunities," *Food Technology* 51:61-74 (1997).

Lourdin, et al., "Influence of Amylose Content on Starch Films and Foams," *Carbohydrate Polymers* 27:261-270 (1995).

Kester, et al., "Edible Films and Coatings: A Review," *Food Technology* 40:47-59 (1986).

(Continued)

*Primary Examiner*—Shaojia Anna Jiang
*Assistant Examiner*—Ganapathy Krishnan
(74) *Attorney, Agent, or Firm*—Womble Carlyle Sandridge & Rice, PLLC

(57) ABSTRACT

A film-forming composition comprising a hydrocolloid, a plasticizer, and water is described. A process and apparatus for producing a non-gelatin film comprising a hydrocolloid, a plasticizer, and water is also disclosed. The process includes combining at least one non-gelatin hydrocolloid, water, and at least one plasticizer into a substantially homogeneous film-forming composition comprising at least about 40 percent water by weight. A substantial portion of the water is then extracted from the film-forming composition to form a dried portion having a water content of less than or equal to about 25 percent by weight. The dried portion of the film-forming composition is formed into a film. A film produced according to the process preferably has a tensile strength at rupture of at least about 0.4 N/mm$^2$, and a percent elongation of at least about 50 percent at rupture at room temperature. An apparatus for performing the process is also described, as well oral dosage forms encapsulated or enrobed in the produced film.

223 Claims, 5 Drawing Sheets

U.S. PATENT DOCUMENTS

| | | | |
|---|---|---|---|
| 5,726,008 A | 3/1998 | Maskasky | 430/569 |
| 5,756,123 A | 5/1998 | Yamamoto et al. | 424/451 |
| 5,804,243 A | 9/1998 | Loh et al. | 426/552 |
| 5,811,388 A | 9/1998 | Friend et al. | 514/2 |
| 5,817,323 A | 10/1998 | Hutchinson et al. | 424/439 |
| 5,932,639 A | 8/1999 | Eden et al. | 524/48 |
| 5,962,053 A | 10/1999 | Merritt, II | 426/138 |
| 5,976,586 A | 11/1999 | Feller | 426/89 |
| 6,030,641 A | 2/2000 | Yamashita et al. | 424/451 |
| 6,063,915 A | 5/2000 | Hansen et al. | 536/114 |
| 6,066,368 A | 5/2000 | Billmers et al. | 427/393.4 |
| 6,099,858 A * | 8/2000 | Morton et al. | 424/456 |
| 6,143,324 A | 11/2000 | Michaud et al. | 242/465 |
| 6,146,570 A | 11/2000 | Stern | 264/141 |
| 6,183,845 B1 | 2/2001 | Ikemoto | 428/213 |
| 6,210,709 B1 | 4/2001 | Laba et al. | 424/451 |
| 6,214,376 B1 | 4/2001 | Gennadios | 424/451 |
| 6,331,205 B1 | 12/2001 | Paris et al. | 106/205.9 |
| 6,340,473 B1 | 1/2002 | Tanner et al. | 242/451 |
| 6,375,981 B1 | 4/2002 | Gilleland et al. | 424/452 |
| 6,517,865 B2 | 2/2003 | Cade et al. | 424/451 |
| 6,528,088 B1 | 3/2003 | Gilleland et al. | 424/451 |
| 6,582,727 B2 | 6/2003 | Tanner et al. | 424/451 |
| 6,607,748 B1 | 8/2003 | Alenaerts et al. | 424/464 |
| 6,745,546 B2 | 6/2004 | Tanner et al. | 53/560 |
| 6,790,495 B1 | 9/2004 | Tomka et al. | 428/35.2 |
| 2002/0081331 A1 | 6/2002 | Tanner et al. | 424/451 |
| 2002/0085487 A1 | 7/2002 | Von Wendorff | 370/216 |
| 2002/0142031 A1 | 10/2002 | Gilleland et al. | |
| 2002/0155200 A1 | 10/2002 | Macquarrie | 426/250 |
| 2002/0187185 A1 | 12/2002 | Jones | 424/452 |
| 2004/0060258 A1 | 4/2004 | Stolz | 53/266.1 |
| 2004/0071808 A1 | 4/2004 | Peter et al. | 425/133.5 |
| 2005/0008677 A1 | 1/2005 | Modliszewski et al. | 424/439 |
| 2005/0013847 A1 | 1/2005 | Ballard et al. | 424/439 |
| 2005/0014852 A1 | 1/2005 | Sewall et al. | 516/99 |
| 2005/0019294 A1 | 1/2005 | Modliszewski et al. | 424/70.13 |
| 2005/0019295 A1 | 1/2005 | Ballard et al. | 424/70.13 |
| 2005/0019374 A1 | 1/2005 | Modliszewski et al. | 424/439 |

FOREIGN PATENT DOCUMENTS

| | | | |
|---|---|---|---|
| EP | 0 169 319 B1 | | 1/1986 |
| EP | 0328317 | | 8/1989 |
| EP | 0 408 503 B1 | | 1/1991 |
| EP | 0 409 782 B1 | | 1/1991 |
| EP | 0 409 788 B1 | | 1/1991 |
| EP | 0 471 558 A2 | | 2/1992 |
| EP | 0 400 484 B1 | | 1/1994 |
| EP | 0622408 | | 2/1994 |
| EP | 0 409 781 B1 | | 6/1994 |
| EP | 0 761 691 A2 | | 3/1997 |
| EP | 0 547 551 B1 | | 11/1997 |
| EP | 0 633 896 B1 | | 6/1998 |
| EP | 1216680 | | 6/2002 |
| EP | 1258242 | | 11/2002 |
| JP | 50-105766 | * | 8/1975 |
| JP | 50105766 | | 8/1975 |
| JP | 50105767 | | 8/1975 |
| JP | 63118229 | | 5/1988 |
| JP | 3121825 | | 5/1991 |
| JP | 3127945 | | 5/1991 |
| JP | 3190709 | | 8/1991 |
| JP | 03190709 | * | 8/1991 |
| JP | 4089841 | | 3/1992 |
| JP | 07196478 | | 1/1995 |
| JP | 7062160 | | 3/1995 |
| JP | 2000127225 | | 5/2000 |
| WO | WO94/25493 | | 11/1994 |
| WO | WO 97/49762 | | 12/1997 |
| WO | WO 99/07347 | | 2/1999 |
| WO | WO 00/10538 | | 3/2000 |
| WO | WO 00/18835 | | 4/2000 |
| WO | WO 01/03677 | * | 1/2001 |
| WO | WO 01/03677 A1 | | 1/2001 |
| WO | WO 01/37817 A1 | | 5/2001 |
| WO | WO 01/91721 A2 | | 12/2001 |
| WO | WO 02/07711 | | 1/2002 |
| WO | WO/ 02/49572 | | 6/2002 |
| WO | WO 02/053088 | | 7/2002 |
| WO | WO 03/009832 | | 2/2003 |
| WO | WO 03061633 | | 7/2003 |
| WO | WO 2004/091527 | | 10/2004 |
| WO | WO 2004/091528 | | 10/2004 |
| WO | WO 2004/091529 | | 10/2004 |
| WO | WO 2004/091530 | | 10/2004 |
| WO | WO 2004/091532 | | 10/2004 |
| WO | WO 2004/091533 | | 10/2004 |
| WO | WO 2004/091537 | | 10/2004 |
| WO | WO 2004/091538 | | 10/2004 |
| WO | WO 2004/091539 | | 10/2004 |

OTHER PUBLICATIONS

Shih, "Effects of Additives on the Development of Edible Films," *Chemistry of Novel Foods*, Chapter 14, 1995 International Chemical Congress of Pacific Basin Societies, Honolulu, Hawaii (Dec. 17-22, 1995).

Bergthaller, et al., "Potato Starch Technology," *Starch/Stärke* 51:235-242 (1999).

BeMiller, et al., "Carbohydrates," *Food Chemistry*, pp. 205-223 (No Date).

"The Birth of a Paintball," *R.P. Scherer Paintballs—How Paintballs are . . .*, pp. 1-2 (1998).

Picullel, "Gelling Carrageenans," *Food Polysaccharides and Their Applications*, pp. 205, 210-212, 233-234 (1995).

Rochas, et al., "Relation Between the Molecular Structure and Mechanical Properties of Carrageenan Gels," *Carbohydrates Polymers* 10:115-127 (1989).

Hermansson, et al., "Effects of Potassium, Sodium and Calcium on the Microstructure and Rheological Behaviour of Kappa-Carrageenan Gels," *Carbohydrate Polymers* 16:297-320 (1991).

Arvanitoyannis, et al., "Edible Films Made from Hydroxypropyl Starch and Gelatin and Plasticized by Polyols and Water," *Carbohydrate Polymers* 36:105-119 (1998).

Derwent Abstract WO 9923118 A1.
Derwent Abstract JP 5148388 A.
Derwent Abstract WO 9304670 A.
Derwent Abstract JP 5004914 A.
Derwent Abstract WO 9218014 A.
Derwent Abstract WO 9206672 A.
Derwent Abstract EP 471558 A.
Derwent Abstract WO 9200731 A.
Derwent Abstract EP 400484 A.
Derwent Abstract JP 63170310 A.
Derwent Abstract EP 273823 A.
Derwent Abstract JP 61009258 A.
Derwent Abstract JP 60037966 A.
Derwent Abstract JP 72023384 B.
U.S. Appl. No. 09/585,846, filed Jun. 1, 2000.

*Food Product Design*, Hegenbart article "Bind for Glory: Designing Foods Using Gums," pp. 21, 24, 26, 29, 32, 35, 38, 42, (Jan. 1993).

Chandrasekaran, R., et al., "Molecular architectures and functional properties of gellan gum and related polysaccharides," *Trends in Food Science & Technology*, vol. 6, pp. 143-148, (May 1995).

Hegenburt, S., "Understanding Carrageenan," *Food Product Design*, vol. 4(3), pp. 109-120, (Jun. 1994).

Sanderson, G. R. et al., "Gellan Gum," *Food Technology*, pp. 63-70 (Apr. 1983).

Nishinari, K. et al., "Characterization and properties of gellan-κ-carrageenan mixed gels," *Food Hydocolloids*, vol. 10(3), pp. 277-283, (1996).

Oakenfull, D. et al., "Rheological and thermal properties of milk gels formed with κ-carrageenan and sodium caseinate," *Food Hydrocolloids*, vol. 13, p. 529, (1999).

Morris, V. J. et al., "Gelation of polysaccharides," *Functional Properties of Food Macromolecules*, p. 168, available as of the filing date.

"VegaGels: Technical Information," Swiss Caps, 2000.

Wilkinson, P.K., "Softgels: manufacturing and considering, in Specialized Drug Delivery Systems," *Manufacturing and Production Technology*, Praveen Tyle, Ed., p. 431, 1990.

Invitation to Pay Additional Fees; International Searching Authority; dated Jan. 25, 2005.

PCT Notification concerning Transmittal of International Preliminary Report on Patentability (Chapter 1 of the Patent Cooperation Treaty), Jan. 24, 2006.

* cited by examiner

NON-GELATIN FILM AND METHOD AND APPARATUS FOR PRODUCING SAME

RELATED APPLICATIONS

This application is a continuation-in-part of application Ser. No. 10/051,201, filed Jan. 18, 2002 now U.S. Pat. No. 6,949,256.

FIELD OF THE INVENTION

The present invention relates to the field of film-forming or gel-forming compositions, and more particularly to substitutes for mammalian-based gel forming materials used in the manufacture of softgels and gelcaps, and a method and apparatus for producing a non-animal edible film of a type that is suitable for enrobing and/or encapsulating oral dosage forms.

BACKGROUND

Gelatin has a wide range of commercial utility. For example, gelatin is used in wet processed photographic emulsions, pharmaceutical dosage forms, cosmetics (binder), and a wide range of food products. Gelatin has many useful physical and chemical properties that support this broad range of utility.

Gelatin is manufactured by the hydrolysis of animal by-products that contain collagen. This is usually found in animal bones, skins, and connective tissue. The collagen containing material is heated in water and the liquor produced is concentrated and dried, leaving behind the colorless or pale yellow protein that constitutes the hydrophilic colloid material known as gelatin.

The primary sources of gelatin are from bovine and swine animals. Additionally, fish and poultry are alternative small volume sources of gelatin. The source of gelatin can be a problem for potential areas of use or for particular consumers. Large groups around the world choose not to ingest any products of pigs (e.g., vegetarians, Hebrews, and Muslims) or the products of beef (e.g., vegetarians and Hindus). As medication and/or diet supplements are provided in gelatin capsules without any indication of the source of the gelatin, the use of capsules is restricted in areas where religious beliefs question the source of the gelatin. Additionally, due to reported possibilities of cross-contamination of diseases among species, for example bovine spongiform encephalopathy ("BSE" or "Mad Cow Disease"), the use of uncontrolled by-products from animals has lost some level of commercial acceptance. In short, there is a need for replacement compositions for gelatin that are not derived from animal sources.

Gelatin is a protein hydrocolloid. Hydrocolloids are hydrophilic colloidal materials that readily absorb water. Types of non-gelatin hydrocolloids include plant exudates, seaweed extracts, plant seed gums or mucilages, cereal gums, fermentation gums, modified cellulose, and modified starches. Non-gelatin hydrocolloids suitable for inclusion in a film-forming composition according to the invention include, but are not limited to, carrageenan, alginates, agar, guar, pectin, locust bean gum, xanthan gum, unmodified starch, modified pregelatinized starch, and gellan gum. Carrageenan is particularly useful in producing a non-gelatin film according to the invention.

Carrageenan is a natural polysaccharide hydrocolloid derived from red seaweed of the species Rhodophycea. Carrageenan is a carbohydrate polymer of repeating galactose and 3,6-anhydrogalactose (sugar) units that is linear and without significant numbers of branches or substitutions. Most, if not all, of the galactose units on a carrageenan molecule possess a sulfated ester group. The exact position of the sulfate groups, the cations on the sulfate groups, and the possible presence of an anhydrous bridge on the molecule differentiate the various types of carrageenan.

There are five distinct types of carrageenan, each of which behaves differently and has distinct properties. The types of carrageenan are iota, kappa, lambda, mu and nu carrageenan. These types of carrageenan can significantly vary in properties. For example, lambda carrageenan in solution is unable to associate into a structure, and therefore is unable to form a gel, but nonetheless acts as a thickener. Both kappa and iota carrageenan, the predominant carrageenan types, are capable of forming gels. Kappa carrageenan is known to form strong gels in the presence of potassium cations. However, kappa carrageenan gels tend to be brittle and exhibit syneresis (exudation of the liquid portion of the gel). Iota carrageenan tends to react strongly to calcium cations and forms a weaker and more flexible gel than kappa carrageenan. Iota carrageenan is not as susceptible to syneresis as kappa carrageenan. Mu and nu carrageenan are thought to be precursors of kappa carrageenan and iota carrageenan, respectively, and may be present only in very small quantities as impurities in pure kappa and iota carrageenan. Mu and nu carrageenan are not of commercial importance.

The type of carrageenan used affects the physical properties of the final gel or film. WO 99/07347 and WO 01/03677 describe gel forming compositions that have iota carrageenan as the sole gelling agent. Despite the fact that kappa carrageenan is also able to gel, these publications teach that kappa carrageenan is detrimental when the end product desired is a film for capsule manufacture, The phenomenon of syneresis and the fact that kappa carrageenan forms brittle gels are cited as reasons for avoiding the use of kappa carrageenan in such films.

When forming a film for subsequent use in medicinal, cosmetic, or nutritional capsule manufacture, the resultant physical properties of sealability, extensibility, and tensile strength are important. Thus, a gelling composition comprising carrageenan or other non-gelatin hydrocolloids must provide adequate physical properties useful in manufacturing. Kappa carrageenan is a less expensive starting material as compared to iota carrageenan. Thus, it would be beneficial to develop a gel- or film-forming composition comprising kappa carrageenan and iota carrageenan, wherein the resultant film provides the requisite physical properties for capsule manufacture.

Processes to manufacture capsules from carrageenan and starch-based shell materials have been very limited. By nature, commercial powder forms of carrageenans and other hydrocolloids require a large percentage of water to fully hydrate. Unfortunately, the strength of a film made from these materials at a water content necessary to fully hydrate the hydrocolloids is not as strong as desired for use in established enrobement and encapsulation processes. To facilitate production of edible films in a production environment, it is sometimes beneficial to add additional amounts of water to a film-forming formula than is strictly required to hydrate the hyrdrocolloids. This additional water reduces the viscosity of the mixture, thereby permitting the mixture to flow under gravity for subsequent processing. Unfortunately, this high water content substantially reduces the strength of films produced from such the mixture.

One method of producing non-gelatin films includes casting these materials at high water content into a film, then drying the film prior to use for encapsulation. Unfortunately, such processes are less than optimal due to the long time that is required to dry the films to a usable level for encapsulation. For this reason, production quantities of capsules have not been made using such a process. Other methods for producing non-gelatin films do not include a drying step prior to encapsulation. Instead, high volumes of carrageenan (approximately 10%) are used to achieve the strength required for capsule manufacture. Such high quantities of carrageenan are undesirable, however, due to the high cost of the material. Such a process also limits the variations in film formula that are available to produce capsules with specific properties such as hardness. Such a process also include a melt on demand system that utilizes a pressurized system to help move the film material to a transfer pump to be processed. This pressurized system is necessary because the high quantity of carrageenan used in the film formula gives the mass a very high viscosity. The pressurized process is also necessary because the gel temperature of the film-forming material at high concentrations of carrageenan necessarily is very high. Unfortunately, holding the mass at this high temperature for an extended period of time as is typically required for production encapsulation causes an undesirable breakdown of the hydrocolloids in the film-forming mixture.

Accordingly, there is a need for a process that permits the use of a variety of types and concentrations of hydrocolloids and permits the viscosity of a film-forming composition to be sufficiently low such that the composition can flow under gravity. It is also desirable to have a process for producing films comprising many types of hydrocolloids that permits a film-forming composition comprising such hydrocolloids to be processed at temperatures that do not cause substantial degradation of the film-forming materials.

SUMMARY OF THE INVENTION

The present invention includes a method of producing a non-gelatin film. The method includes combining at least one non-gelatin hydrocolloid, water, and at least one plasticizer into a substantially homogeneous film-forming composition comprising at least about 40 percent water by weight. The method further includes extracting a portion of the water from the film-forming composition to form a dried portion having a water content of less than or equal to about 25 percent by weight. The method also includes forming the dried portion of the film-forming composition into a film. A1

The invention also includes a method of producing a non-gelatin film that includes combining at least one non-gelatin hydrocolloid, water, and at least one plasticizer into a substantially homogeneous film-forming composition having a water content of at least about 40 percent by weight. This method further includes extracting a portion of the water from the film-forming composition to form a dried portion, and forming the dried portion of the film-forming composition into a film. A film produced by such a method and having a width of about 20 mm and a thickness of about 0.6 mm has a tensile strength at rupture of at least about 5 N (or about 0.4 Newtons per square millimeter ($N/hmn^2$)) at room temperature as measured using a texture analysis machine such as a TA-XT2 Texture Analyzer by Stable Micro Systems (Surrey, UK).

The invention further includes a method of producing a non-gelatin film including combining at least one non-gelatin hydrocolloid, water, and at least one plasticizer into a substantially homogeneous film-forming composition comprising at least about 40 percent water by weight. A portion of the water is extracted from the film-forming composition to form a dried portion, and the dried portion of the film-forming composition is formed into a film having a percent elongation of at least about 50 percent at rupture at room temperature.

In addition, the invention includes a method of producing a non-gelatin film including combining at least one non-gelatin hydrocolloid, water, and at least one plasticizer into a substantially homogeneous film-forming composition having a viscosity of less than about 100,000 cP as measured at a temperature less than about 100 degrees C. The method further includes extracting a portion of the water from the film-forming composition to form a dried portion having a water content less than or equal to about 25 percent by weight, and forming the dried portion of the film-forming composition into a film.

The invention also includes a method of producing a non-gelatin film that includes combining at least one non-gelatin hydrocolloid, water, and at least one plasticizer into a substantially homogeneous film-forming composition having a viscosity of less than about 100,000 cP as measured at a temperature less than about 100 degrees C. The method further includes extracting a portion of the water from the film-forming composition to form a dried portion, and forming the dried portion of the film-forming composition into a film, wherein the film has a tensile strength at rupture of at least about 5 N at room temperature.

In another method according to the invention, the method includes combining at least one non-gelatin hydrocolloid, water, and at least one plasticizer into a substantially homogeneous film-forming composition having a viscosity of less than about 100,000 cP as measured at a temperature less than about 100 degrees C., and then extracting a portion of the water from the film-forming composition to form a dried portion. The dried portion of the film-forming composition is formed into a film having a percent elongation of at least about 50 percent at rupture at room temperature.

These and other aspects of the invention will be apparent to those skilled in the art from a reading of the following description of embodiments of the invention together with the drawings. The embodiments as set forth herein are not intended to limit the scope of the invention, which is intended to cover equivalent materials, methods, devices, and compositions as set forth in the appended claims.

DETAILED DESCRIPTION

Figure 1:
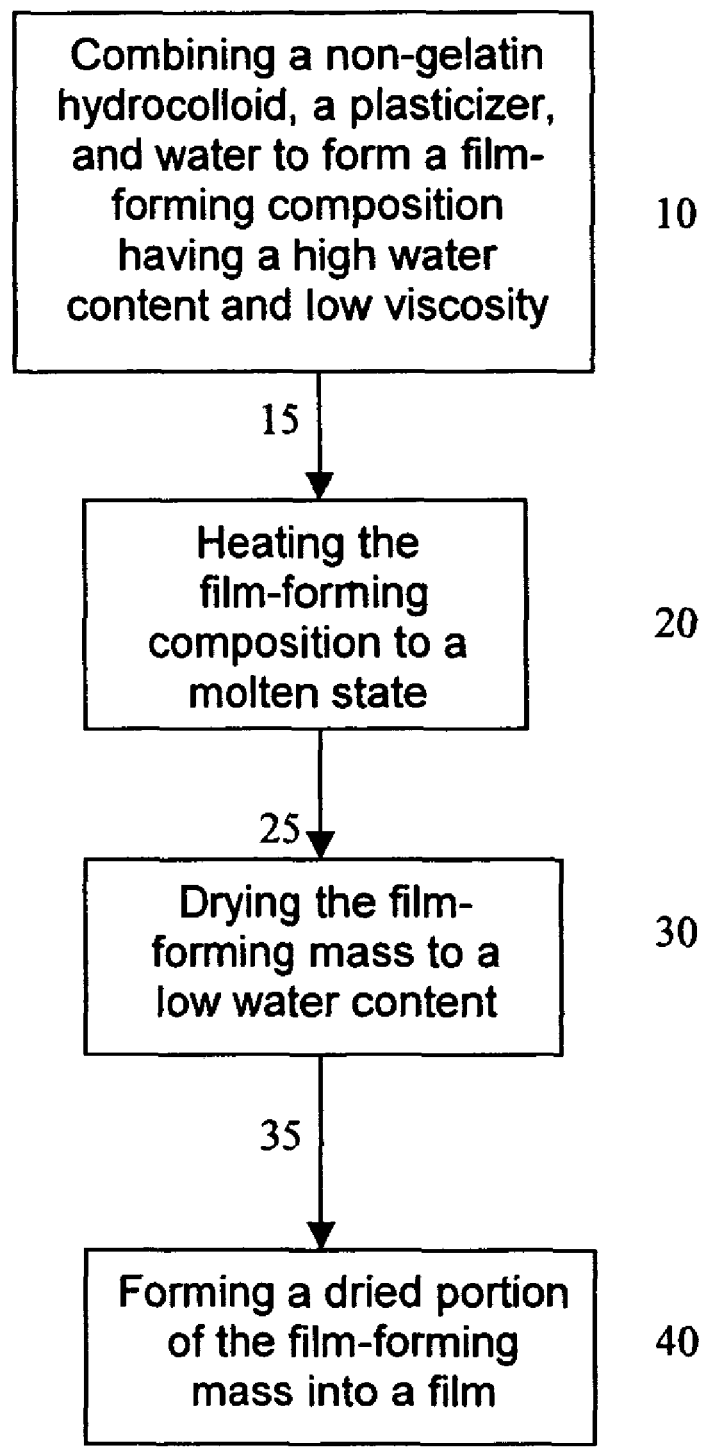
FIG. 1 is a flow chart showing a process for producing an edible non-gelatin film.

Formulations, methods, and devices for the manufacturing of non-animal based hydrocolloid film-forming compositions are described. The film-forming composition may be used for encapsulation of dosage forms in liquid, solid, gel, paste, compacted powder, or suspension form. Such dosage forms can include medicinal, pharmaceutical, nutritional or dietetic drug dosage forms, as well as cosmetics, paints, bath products or other desirably encapsulated dosage forms.

As used herein, the term "softgel" means a soft gelatin capsule, in agreement with the accepted nomenclature adopted by the SoftGel Association. Formerly, the accepted nomenclature was a soft elastic gelatin (SEG) capsule. Generally, a softgel is a one-piece, sealed, soft gelatin (or other film-forming material) shell that contains a solution, a suspension, or a semi-solid paste.

Other encapsulated dosage forms are known to practitioners in the art and include, but are not limited to, caplets such as SOFLET™ gelatin-enrobed hard tablets made by Banner Pharmacaps, Inc.

The phrase "dosage form" as used herein encompasses any material or composition in a form suitable for encapsulation by the film-forming composition described herein. Thus, a dosage form can be a pharmaceutical or nutritional composition, or a cosmetic, paint, soap, bath oil or other desirably encapsulated product. The dosage form can be a solid, liquid, gel, compacted powder, suspension or any other form suitable for encapsulation.

The term "encapsulated dosage form" refers to any dosage form encapsulated with a non-animal hydrocolloid film-forming composition as set forth herein. The encapsulated dosage form can be in any form known to practitioners in the art, such as but not limited to a softgel or caplet.

The terms "enrobe" and "encapsulate" as used herein mean placing a dosage form inside of a film-forming composition, such that the dosage form is completely surrounded by the film-forming composition. By methods known to practitioners in the art, the dosage form can be inserted into the film-forming composition in some manner, or the film-forming composition can be wrapped around the dosage form.

A "capsule shell" as used herein refers to the film-forming composition described herein when used to encapsulate a substance such as a drug dosage form.

"Capsule" refers to a softgel, caplet, or any other encapsulated dosage form known to practitioners in the art, or a portion thereof.

The phrase "solids content" as used herein refers to the ratio of the weight of the dry film-forming composition components to the total weight of the composition, expressed as a percentage.

The adjective "dry" or "dried" as used herein means relatively free of water or other liquids. The verb "dry" refers to the act of making dry or more dry such as by extracting or removing water.

Manufacture of uniform capsule shells requires a film-forming composition that has good "machineability," i.e., it is important that the film-forming composition in a preferred embodiment be able to be brought into contact with rollers or other machine parts during processing without sticking onto these machine parts. However, some stickiness is required for proper seam formation and, in the manufacture of caplets, to improve contact between the encapsulating material and the solid tablet core.

Physical characteristics for proper machineability of the film-forming composition described herein during film formation, capsule shell formation and encapsulation of a dosage form, regardless of the method or machine used, include desirable extensibility, sealability, viscosity and tensile strength at rupture of the film-forming composition as known to practitioners in the art.

The term "extensibility" as used herein defines the increase in length of the film-forming composition set forth herein on application of a tensile force (pull). The term "percent elongation" is also used herein to refer to this property. A preferable maximum increase in length at rupture for a 50 mm long film of about 20 mm wide is at least about 50% of the unstretched length at rupture. Preferably, a 50 mm long film elongates between about 20 mm and about 80 mm, and most preferably between about 35 mm and about 70 mm.

The term "sealability" refers to the ability of one or more film of the film-forming composition set forth herein to fuse together using methods known to practitioners in the art, such as but not limited to the application of heat and/or pressure. The seam that is created in the film upon fusing should be continuous and strong to prevent leakage of encapsulated dosage forms.

The tensile strength at rupture of a film made from one embodiment of a film-forming composition as set forth herein having a moisture content of between about 5% and about 20% is preferably between about 5 N and about 100 N, and most preferably between about 10 N and about 80 N, as measured by methods known to practitioners in the art. One suitable means of measuring the tensile strength at rupture is by use of a TA-XT2 Texture Analyzer by Stable Micro Systems (Surrey, UK).

One embodiment of a film-forming composition comprises a blend of iota and kappa carrageenan, thus overcoming the recognized deficiencies of kappa carrageenan. A film-forming composition having the desired physical properties of extensibility, sealability, viscosity and tensile strength at rupture is provided. The kappa carrageenan provides gel strength while the iota carrageenan provides flexibility to the hydrocolloid film. No additional gelling salts or processing aids, such as surfactants or buffers, are necessary for producing a suitable film-forming composition of the invention. Thus, due to the use of less expensive starting materials and fewer ingredients, the film-forming composition set forth herein provides a more cost effective film-forming material than heretofore available.

An embodiment of a film-forming composition according to the invention comprises from about 1% to about 15% by weight commercially available iota carrageenan, such as but not limited to TIC Pretested® COLLOID 881M, available from TIC Gums of Belcamp, Md. Other available forms of iota carrageenan as known to practitioners in the art are also suitable for use herein. In such an embodiment, iota carrageenan preferably is present in an amount of from 2% to about 10% by weight of the composition, and more preferably in an amount of from 2.5% to about 7.5% by weight of the composition.

An embodiment of the film-forming composition also comprises kappa carrageenan in an amount less than or equal to 50% by weight of total carrageenan in the film-forming composition. Preferably, in this embodiment, kappa carrageenan is present in an amount of less than or equal to about 100% by weight of iota carrageenan, more preferably in an amount less than about 100% by weight of iota carrageenan, provided the total amount of carrageenan does not exceed 20% by weight of the composition. Kappa carrageenan is present in an amount of from about 0.1% to about 15% by weight of the composition, and more preferably in an amount of from about 0.5% to about 7.5% by weight of the composition. Kappa carrageenan from any commercial source is acceptable, such as TIC Pretested® COLLOID 710H, available from TIC Gums of Belcamp, Md. Other commercial sources of kappa carrageenan as known to practitioners in the art are also suitable for use herein.

A mixture of kappa carrageenan and a glucomannan such as but not limited to konjac flour, as known to practitioners in the art, may be used in place of some or all of the kappa carrageenan in a composition according to the invention. One example of such a mixture is NUTRICOL® GP751, a commercially available blend of kappa carrageenan and konjac flour, sold by FMC Biopolymer of Philadelphia, Pa. Other blends of kappa carrageenan and glucomannans as known to practitioners in the art are also suitable for use herein in place of some or all of the kappa carrageenan.

The total amount of carrageenan in one embodiment of the composition is less than or equal to about 20% by weight of the composition. Preferably, the total amount of carrageenan is less than or equal to about 10% by weight of the composition.

Other hydrocolloids as known to practitioners in the art optionally can be present in an embodiment of the composition in limited amounts. In such an embodiment, the total amount of all hydrocolloids, including the carrageenans but excluding bulking agents, preferably does not exceed 22% by weight of the composition. Preferably, such hydrocolloids may include viscosity agents that can modify the physical properties of the final gel or film. Practitioners in the art appreciate that adding plant-based hydrocolloids and gums to a film-forming composition can increase the viscosity of the composition. Viscosity agents suitable for use in an embodiment of the composition disclosed herein include, but are not limited to alginates, guar, pectin, locust bean gum, xanthan gum, agar, unmodified starch, modified pregelatinized starch, gellan gum and other viscosity agents known to practitioners in the art. Hydrocolloids acting as viscosity agents optionally may be added to the film-forming composition in amounts less than or equal to about 2% by weight of the composition to increase the viscosity of the composition.

The hydrocolloids, including those used as viscosity agents but excluding those used as bulking agents and carrageenans, can be present in an embodiment of the composition in an amount less than 100% by weight of the amount of iota carrageenan, preferably in an amount less than or equal to the amount of kappa carrageenan, and most preferably in an amount less than 2% by weight of the composition. The total amount of all hydrocolloids, including the carrageenans but excluding bulking agents, preferably does not exceed 22% by weight of the composition.

In one embodiment of a film-forming composition according to the invention, the composition comprises a bulking agent, such as a modified starch. The bulking agent increases the solids content of the film-forming composition, thereby contributing to a reduction in the amount of energy and time necessary to dry the film-forming composition once formed into a capsule or capsule shell. Such a bulking agent preferably is a low viscosity modified starch that contributes only minimally to gel formation, but serves to increase film strength and sealability of the film-forming composition, and reduces water content in the wet formulation. Further, the bulking agent provides some adhesiveness, minimizes syneresis of the kappa carrageenan, improves seam formation and increases viscosity of the film-forming composition. Preferably, the bulking agent is a low viscosity starch ether or esterified starch as known to practitioners in the art, such as but not limited to N-LOK® (starch sodium octenyl succinate), a modified waxy maize starch with corn syrup solids added, sold by National Starch & Chemical Company of Bridgewater, N.J. Preferably, the modified starch is potato, corn, or maize based. Optionally, up to 30% of the modified starch can be replaced with conventional unmodified starch and/or modified pregelatinized starch such as, but not limited to, Ultra Sperse® M by National Starch and Chemical Company of Bridgewater, N.J. The film-forming composition has a weight ratio of bulking agent to total carrageenan of from about 1:1 to about 20:1, and preferably from about 2:1 to about 15:1. The bulking agent comprises from about 10% to about 60% by weight of the total film-forming composition and preferably from about 15% to about 50% by weight of the total film-forming composition. Those skilled in the art will recognize other bulking agents, such as but not limited to modified pregelatinized starch, guar gum, gum arabic and locust bean gum, can be used in the composition. However, severely hydrolyzed starches and dextrins are not recommended for use in the composition.

An embodiment of a film-forming composition according to the invention may further comprise one or more plasticizer selected from those known to practitioners in the art. A plasticizer provides extensibility and improved sealability in the film-forming composition, allowing for formation of strong seams during encapsulation of a dosage form. Also, plasticizers reduce the tensile strength of films made from the film-forming composition. A preferable plasticizer is a combination of sorbitol syrup and maltitol syrup, most preferably a combination of a non-crystallizing sorbitol syrup, such as SORBITOL SPECIAL™ acquired from SPI Polyols of New Castle, Del., and LYCASIN®, a maltitol syrup acquired from Roquette of Keokuk, Iowa. Non-crystallizing sorbitol is preferable over regular sorbitol because regular sorbitol is believed to cause blooming in capsules, a defect where white crystals form on the surface of capsules during storage. Acceptable substitutes for non-crystallizing sorbitol include other plasticizers as known to practitioners in the art, such as but not limited to glycerin, polyethylene glycol and combinations thereof. The amount of plasticizer used in the film-forming composition is from about 10% to about 50% by weight of the total film-forming composition, and preferably from about 12% to about 36% by weight of the total film-forming composition.

An embodiment of a film-forming composition according to the invention comprises water in an amount sufficient to bring the total composition to 100% by weight. Generally, water is present in an amount from about 10% to about 90% by weight of the composition. Preferably, water is present in an amount of from about 14% to about 79% by weight of the composition, and more preferably from about 20% to about 60% by weight of the composition. Preferably, the water is distilled water. If the film-forming composition is used to form medicinal, nutritional or other softgels or caplets intended for human use or consumption, purified distilled water is preferable.

As known to practitioners in the art, a film-forming composition according to the invention can also contain other ingredients, such as taste modifiers, opacifying and coloring agents, preservatives, and similar additives that do not significantly alter film-forming capabilities. The additives can be added in any amount known to practitioners in the art to achieve the desired effect without altering the film-forming properties of the composition. Preferably, the total amount of all additives does not exceed about 5% by weight of the composition, more preferably, it does not exceed about 2% by weight of the composition.

In one embodiment, the solids content of the wet film-forming composition is from about 11% to about 90% by weight of the wet composition, preferably from about 40% to about 90% by weight, most preferably from about 50% to about 80% by weight of the wet composition.

The preferred physical characteristics of the wet film-forming composition are based upon the encapsulation of dosage forms using encapsulation machinery as known to practitioners in the art. One method of capsule production known in the art uses a rotary die process in which a molten mass of a gelatin film-forming composition is fed from a reservoir onto cooled drums to form two spaced sheets or ribbons in a semi-molten state. These sheets are fed around rollers and brought together at a convergent angle into the nip of a pair of roller dies that include opposed die cavities. A dosage form is fed into the wedge-shaped joinder of the sheets. The sheets are continuously conveyed between the dies, with the dosage form to be encapsulated, such as a medicament, being trapped between the sheets inside the die cavities. The sheets are then pressed together ("sealed"), and severed around each die so that opposed edges of the sheets seal together to encapsulate or enrobe the dosage form, forming a capsule. The part of the sheet that is severed from the segments forming the capsules is collected and either discarded or recycled, depending on the content of the dosage form. The capsules may be finally dried to increase the film integrity and packaged for later distribution and sale. Other encapsulating machines and methods applicable for use with the film-forming composition described herein are known to practitioners in the art, such as but not limited to the method of enrobing hard tablets (SOFLET™) as disclosed and claimed in U.S. Pat. Nos. 5,146,730 and 5,549,983.

In one embodiment of a process for forming a capsule using a film forming composition as described herein, a film-forming composition is first formed by mixing all materials together and heating with stirring until a smooth liquid, free of particulates, is formed. Preferably, hydrocolloids comprising kappa and iota carrageenan are mixed together with a bulking agent and any other dry optional ingredients. A plasticizer is added with mixing to the dry mix. Water is then added with continued mixing and the entire mixture is heated until the ingredients are uniformly dispersed. Additives such as colorants, opacifiers, preservatives, flavorants and the like as known to practitioners in the art can be added as desired during the mixing process.

In one embodiment, all the dry ingredients (kappa carrageenan, iota carrageenan, and bulking agent, as well as dry additives) are blended together to form a dry mix. In a separate container, water and plasticizer, as well as any liquid additives, are mixed together as a liquid mix and heated to at least about 75° C., preferably about 90° C. While stirring the hot liquid mix, the dry mix is slowly added to the hot liquid mix to minimize formation of large lumps. The dispersion formed is heated with mixing to a temperature of from about 85° C. to about 95° C. The temperature is maintained with mixing until the film-forming composition melts to form a smooth liquid free of particulates.

A film-forming composition in liquid form can be subjected to one or more treatments as known to practitioners in the art. The treatments can include casting the liquefied composition into a ribbon or sheet, drying the ribbon, and conditioning it to a predetermined moisture content, typically from about 5% to about 30% moisture by weight of the ribbon, preferably from about 10% to about 20% moisture by weight of the ribbon, as known to practitioners in the art. The dry ribbon or sheet can be stored, or used directly after drying. Preferably, the dry ribbon or sheet is used to encapsulate a dosage form, such as by use of a rotary die encapsulation machine, although other methods of encapsulation as known to practitioners in the art may also be used.

Many non-gelatin film-forming compositions require a high percentage of water included in the composition to allow the hydrocolloids to fully hydrate and/or to allow the composition to be flowable enough for easy use in manufacturing. Most films do not have sufficient strength at such a high water content to be directly usable in a rotary die encapsulation process. Films cast compositions having a high water content take too long to dry to practically be used in a continuous rotary die encapsulation process. Accordingly, it is desirable to lower the water content of such film-forming compositions prior to film formation. In one process according to the invention, a film-forming composition having a high water content and low viscosity is metered into an extruder/dryer to reduce the water content to a level that yields a dried composition that can be readily formed into a usable film. The dried film-forming composition can be continuously extruded into a ribbon, film or other useful profile shape.

Alternatively, some film-forming compositions can be cast into a wet film on the drum of a rotary die encapsulation machine and the wet film used to encapsulate a dosage form. Encapsulated dosage forms include, but are not limited to drug dosage forms, nutritional supplements, cosmetics, bath oils and gels, paint balls and the like.

The film-forming composition can also be formed by adding a dry mix and a liquid mix as defined elsewhere herein to an extruder, wherein the dry and liquid mixes are mixed together and heated, then extruded through dies into sheets, films or tubes. A premixed film-forming composition may also be added to an extruder for extrusion to form sheets, films or tubes. The water content of the film forming composition may be adjusted to the desired level in the extruder. The extruded composition is fed to an encapsulation machine for the manufacture of encapsulated dosage forms. Encapsulated dosage forms include, but are not limited to drug dosage forms, nutritional supplements, cosmetics, bath oils and gels, paint balls and the like.

As used herein, the term "sheet" or "ribbon" is meant to include any form of the film-forming composition suitable for encapsulation of a dosage form as known to practitioners in the art, including but not limited to sheets, films, tubes, hemispheres, cones and the like. Wet cast or extruded ribbons are preferably from 0.4 mm to about 1.0 mm thick, though other thicknesses can be formed and used as known to practitioners in the art. Dry ribbons are typically from about 0.5 mm to about 0.7 mm thick, though thicker or thinner dry ribbons can be formed as known to practitioners in the art. The thickness of a dry or wet ribbon is determinable by a practitioner in the art based on the desired end use. Preferably, the moisture content of the dry ribbon is from about 5% to about 25% by weight of the ribbon, more preferably from about 10% to about 20% by weight of the ribbon.

Once the film-forming composition is formed into the desired shape, it can be used to encapsulate dosage forms including liquids, solids, gels and suspensions, according to methods known to practitioners in the art. Typically, for encapsulation, a film is heated to and maintained at a temperature of from about 60° C. to about 100° C., preferably from about 75° C. to about 95° C., during the encapsulation process. For example, when a rotary die encapsulation machine is used, the film is heated by a wedge that is located above the dies. The film is maintained at a temperature of from about 60° C. to about 99° C., typically from about 75° C. to about 95° C., during encapsulation of the dosage form. Other examples of equipment, heating methods and temperatures therefore are known to practitioners in the art.

During encapsulation, the ribbon is frequently lubricated to prevent adherence to the machinery and prevent entrapment of air bubbles within the capsule. Suitable lubricants are known to practitioners in the art, and include, but are not limited to, triglycerides, mineral oil and acetylated monoglycerides.

Once formed, the capsule shell of dry film-forming composition preferably has a solids content of from about 70% to about 95% by weight of the dry composition. Iota carrageenan is present in an amount of from about 2% to about 20% by weight of the dry composition, and preferably from about 2.5% to about 10% by weight of the dry composition. Kappa carrageenan is present in an amount of from about 0.4% to about 20% by weight of the dry composition, and preferably from about 0.5% to about 10% by weight of the dry composition. The bulking agent is present in an amount of from about 10% to about 80% by weight of the dry composition, and preferably from about 40% to about 70% by weight of the dry composition. The plasticizer is present in an amount of from about 30% to about 60% by weight of the dry composition, and preferably from about 35% to about 50% by weight of the dry composition. The water content is from about 5% to about 30% by weight of the dry composition, and preferably from about 7.5% to about 20% by weight of the dry composition.

Examples of various embodiments of film-forming compositions of the invention are set forth below. Composition components are set forth by weight percentage of the total weight of the composition; "ι" refers to iota carrageenan and "κ" refers to kappa carrageenan.

Kappa carrageenan is nonstandardized carrageenan and iota carrageenan is standardized carrageenan (standardized with maltodextrin) supplied by TIC Gums of Belcamp, Md. Kappa carrageenan is supplied as TIC PRETESTED® COLLOID 710H. Standardized iota carrageenan is supplied as TIC PRETESTED® COLLOID 881M. The modified starch is N-LOK®, starch sodium octenyl succinate with corn syrup solids added, and the modified pregelatinized starch is Ultra Sperse® M, both supplied by National Starch and Chemical Company of Bridgewater, N.J. SORBITOL SPECIAL™ is non-crystallizing sorbitol supplied by SPI Polyols of New Castle, Del. The maltitol used is LYCASIN®, supplied by Roquette of Keokuk, Iowa. Glycerin is USP GLYCERIN acquired from commercial sources such as Henkel of Cincinnati, Ohio. Titanium dioxide is supplied by Warner-Jenkinson Co., Inc., of South Plainfield, N.J. Water is purified, distilled water prepared in house.

EXAMPLE 1

| | |
|---|---|
| Kappa Carrageenan | 2.0% |
| Iota Carrageenan | 2.0% |
| Modified Starch | 20.0% |
| Ratio of starch:total carrageenan | 5:1 |
| Sorbitol Special ™ | 36.0% |
| Distilled Water | 40.0% |

EXAMPLE 2

| | |
|---|---|
| Kappa Carrageenan | 2.0% |
| Iota Carrageenan | 2.0% |
| Modified Starch | 15.0% |
| Ratio of starch:total carrageenan | 7.5:2 |
| Sorbitol Special ™ | 35.0% |
| Titanium Dioxide | 0.5% |
| Distilled Water | 45.5% |

EXAMPLE 3

| | |
|---|---|
| Kappa Carrageenan | 1.0% |
| Iota Carrageenan | 3.0% |
| Modified Starch | 20% |
| Ratio of starch:total carrageenan | 5:1 |
| Sorbitol Special ™ | 30.0% |
| Titanium Dioxide | 1.0% |
| Distilled Water | 45.0% |

EXAMPLE 4

| | |
|---|---|
| Kappa Carrageenan | 2.0% |
| Iota Carrageenan | 3.0% |
| Modified Starch | 20% |
| Ratio of starch:total carrageenan | 4:1 |
| Sorbitol Special ™ | 35.0% |
| Titanium Dioxide | 0.5% |
| Distilled Water | 39.5% |

EXAMPLE 5

| | |
|---|---|
| Kappa Carrageenan | 1.5% |
| Iota Carrageenan | 2.5% |
| Modified Starch | 20.0% |
| Ratio of starch:total carrageenan | 5:1 |
| Glycerin (USP) | 25.0% |
| Titanium Dioxide | 0.5% |
| Distilled Water | 50.5% |

EXAMPLE 6

| | |
|---|---|
| Kappa Carrageenan | 1.5% |
| Iota Carrageenan | 2.5% |
| Modified Starch | 20.0% |
| Ratio of starch:total carrageenan | 5:1 |
| Maltitol | 25.0% |
| Titanium Dioxide | 0.5% |
| Distilled Water | 50.5% |

EXAMPLE 7

| | |
|---|---|
| Kappa Carrageenan | 1.5% |
| Iota Carrageenan | 2.5% |
| Modified Starch | 20.0% |
| Ratio of starch:total carrageenan | 5:1 |
| Glycerin (USP) | 12.5% |
| Sorbitol Special ™ | 12.5% |
| Titanium Dioxide | 0.5% |
| Distilled Water | 50.5% |

EXAMPLE 8

| | |
|---|---|
| Kappa Carrageenan | 1.5% |
| Iota Carrageenan | 2.5% |
| Modified Starch | 25.0% |
| Ratio of starch:total carrageenan | 6.25:1 |
| Maltitol | 5.0% |
| Sorbitol Special ™ | 15.0% |
| Titanium Dioxide | 0.5% |
| Distilled Water | 50.5% |

EXAMPLE 9

| | |
|---|---|
| Kappa Carrageenan | 2.5% |
| Iota Carrageenan | 2.5% |
| Modified Starch | 23.0% |
| Ratio of starch:total carrageenan | 4.6:1 |
| Maltitol | 16% |
| Sorbitol Special ™ | 8% |
| Titanium Dioxide | — |
| Distilled Water | 48% |

EXAMPLE 10

| | |
|---|---|
| Kappa Carrageenan | 1.5% |
| Iota Carrageenan | 3.5% |
| Modified Starch | 25.0% |
| Ratio of starch:total carrageenan | 5:1 |
| Maltitol | 7.0% |
| Sorbitol Special ™ | 13.0% |
| Titanium Dioxide | 0.10% |
| Distilled Water | 49.90% |

EXAMPLE 11

| | |
|---|---|
| Kappa Carrageenan | 1.5% |
| Iota Carrageenan | 3.5% |
| Modified Starch | 25.0% |
| Ratio of starch:total carrageenan | 5:1 |
| Maltitol | 8.0% |
| Sorbitol Special ™ | 15.0% |
| Titanium Dioxide | 0.10% |
| Distilled Water | 46.90% |

EXAMPLE 12

| | |
|---|---|
| Kappa Carrageenan | 2.5% |
| Iota Carrageenan | 2.5% |
| Modified Starch | 40.0% |
| Pregelatinized Starch | 5.0% |
| Ratio of starch:total carrageenan | 9:1 |
| Maltitol | 3.75% |
| Sorbitol Special ™ | 18.75% |
| Titanium Dioxide | — |
| Distilled Water | 27.50% |

The film-forming compositions of examples 1-12 were cast into films and dried to between about 5% and about 15% moisture. The films were cut into strips 20 mm wide by 50 mm long. The films for Examples 2-12 were tested for tensile strength at rupture and extensibility using a TA-XT2 Texture Analyzer manufactured by Stable Micro Systems, (Surrey, UK). The following table charts the tensile strength and extensibility of the resulting films, where the values are mean values with standard deviations taken from four (4) replicates.

TABLE 1

| Example # | Tensile Strength at Rupture (N) | Maximum Extension at Rupture (mm) |
|---|---|---|
| 2 | 10.7 ± 0.2 | 53.1 ± 3.3 |
| 3 | 14.8 ± 0.7 | 63.6 ± 4.7 |
| 4 | 12.9 ± 0.5 | 45.7 ± 2.1 |
| 5 | 5.8 ± 0.4 | 43.2 ± 1.6 |
| 6 | 13.2 ± 1.2 | 51.4 ± 2.2 |
| 7 | 7.1 ± 0.6 | 45.9 ± 8.3 |
| 8 | 15.6 ± 2.4 | 64.9 ± 5.7 |
| 9 | 10.3 ± 0.3 | 42.4 ± 2.2 |
| 10 | 29.7 ± 2.0 | 56.6 ± 2.0 |
| 11 | 18.7 ± 4.5 | 41.4 ± 9.2 |
| 12 | 29.5 ± 0.6 | 59.8 ± 7.2 |

To demonstrate the desirable characteristics for kappa carrageenan, iota carrageenan and bulking agents used in this invention, commercially available kappa carrageenan, iota carrageenan and a modified starch were formed into solutions and their viscosity, gel point, melting point and gel strength were measured. The materials used were as follows:

Kappa Carrageenan: Colloid 710H (Lot #1025) from TIC Gums of Belcamp Md.

Iota Carrageenan: Colloid 881M (Lot #1539) from TIC Gums of Belcamp Md.

Modified Starch (starch sodium octenyl succinate): N-Lok (Lot #FK17502) from National Starch & Chemical Co. of Bridgewater, N.J.

In one procedure for producing a film-forming composition like that described above, a 3% dispersion of carrageenan in purified distilled water was prepared by heating the water to 70° C. and adding the carrageenan with stirring. The dispersion was heated at 70° C. until it became smooth and free of any particulates (non-dispersed carrageenan). Similarly, a 10% dispersion of modified starch in water was prepared.

The viscosity, gelling, holding, frequency and heating (melting) profiles were measured using a mechanical rheometer (AR1000 Advanced Mechanical Rheometer manufactured by TA Instruments of New Castle, Del.) using a 4° steel cone.

Viscosity was measured by shearing the sample at a rate of 0 to 120 per second in two (2) minutes.

The gelling profile was determined by dropping the temperature from 80° C. to 10° C. at 5° C. per minute, with constant strain and frequency of 2% and 1 Hz, respectively. The gelling point was determined to be the temperature at which the storage and loss moduli, G' and G" respectively, crossed. Following gelling, the sample was held at 10° C. for 5 min to obtain a holding profile. After the holding step, the mechanical spectrum (frequency profile) of the gel formed was determined by performing a frequency sweep from 0.1 Hz to 100 Hz at 10° C., with constant strain of 2%. The storage modulus (G') at a frequency of 1 Hz was chosen as the gel strength of the gel formed by the carrageenan dispersion. The gel was then heated at a rate of 5° C. per minute from 10° C. to 95° C. to obtain the melting profile of the gel, with constant strain and frequency of 2% and 1 Hz, respectively. The melting point was determined to be the temperature at which the storage and loss moduli, G' and G" respectively, crossed. The results are set forth in Table 2.

TABLE 2

| Sample | Viscosity (cP) | Gelling point (° C.) | Melting point (° C.) | Gel Strength (Pa) |
|---|---|---|---|---|
| 3% kappa carrageenan dispersion in water | 618.4 | 40.6 | 60.3 | 35,740 |
| 3% iota carrageenan dispersion in water | 93.8 | 61.2 | 64.9 | 976 |
| 1.5% kappa carrageenan + 1.5% iota carrageenan dispersion in water | 206.6 | 47.2 | 70.8 | 19,800 |
| 10% starch sodium octenyl succinate | 3.8 | — | — | — |

The above results are within the desirable ranges for viscosity, gel point, melting point and gel strength for iota carrageenan, kappa carrageenan and a bulking agent. Preferably, the range for these parameters for dispersions of iota carrageenan, kappa carrageenan and a bulking agent as described above are as set forth below in Table 3.

TABLE 3

| Sample | Viscosity (cP) | Gelling point (° C.) | Melting point (° C.) | Gel Strength (Pa) |
|---|---|---|---|---|
| 3% kappa carrageenan dispersion in water | 580-650 | 38-43 | 57-64 | 33,000-38,000 |
| 3% iota carrageenan dispersion in water | 85-100 | 58-65 | 60-69 | 920-1,100 |

TABLE 3-continued

| Sample | Viscosity (cP) | Gelling point (° C.) | Melting point (° C.) | Gel Strength (Pa) |
|---|---|---|---|---|
| 1.5% kappa carrageenan + 1.5% iota carrageenan dispersion in water | 190-220 | 44-50 | 67-75 | 18,000-21,000 |
| 10% starch sodium octenyl succinate | 3-5 | — | — | — |

The invention also includes a method for producing an edible non-gelatin film in accordance with the invention that is particularly adapted for high-volume production. FIG. 1 is a flow chart of one embodiment of a such a method. Constituent ingredients of a non-gelatin film-forming composition comprising carrageenan are mixed 10 together with a high water content. The term "high water content" as used herein means a total water content that permits complete hydration of the hydrocolloid and allows the mass to have a viscosity of less than about 100,000 cP at a temperature less than about 100 degrees C. Preferably the viscosity of the "wet" film-forming composition is less than about 50,000 cP, and most preferably the viscosity is less than about 10,000 cP. A water content of at least about 40 percent by weight has been shown to provide film-forming compositions having preferably low viscosities. The mixture is heated 20 to a viscous molten state. The molten film-forming composition is then at least partially dried 30 such that the moisture content of the film-forming composition is substantially reduced to a low moisture content. The term "low water content" as used herein means the material produced by the process is sufficiently dry to produce a film that is the proper strength and extensibility to be used in a typical encapsulation process. A water content of about 25 percent or less by weight has been shown to produce a useful film according to one embodiment of the process. A dried portion of the film-forming composition is formed into a an edible non-gelatin film such as by extrusion, rolling, or any other suitable method.

Table 1 lists the ingredients of one embodiment of a mixture for use in a process according to the invention as shown in FIG. 1.

TABLE 4

| Ingredient | Approximate Weight Percent |
|---|---|
| Kappa carrageenan | 1.5 |
| Iota carrageenan | 4 |
| Modified starch | 22.2 |
| Sorbitol Special ® | 9.9 |
| Lycasin ® | 4.4 |
| Glycerin | 5.4 |
| Distilled Water | 49.4 |
| Additional Distilled Water | 3.2 |

Other formulas comprising at least one film-forming hydrocolloid, at least one plasticizer, and water may be used in a process according to the invention without departing from the invention.

The kappa carrageenan may be TIC Pretested® COLLOID 710H, and the iota carrageenan may be TIC Pretested® COLLOID 881M, both available from TIC Gums of Belcamp, Md. The modified starch may be Grain Processing Company No. B-793. Sorbitol, especially non-crystallizing sorbitol (such as Sorbitol Special® available from SPI Polol), maltitol syrup (such as Lycasin®), and glycerin may be used as plasticizers, either alone or in combination. Other equivalent ingredients may be substituted. Preferably, the water is purified distilled water.

In one embodiment of the process, mixing the ingredients includes pre-mixing all liquid components except for a portion of the water and glycerin by hand in a container. The mixed liquid components are then preheated to about 200 degrees F. The dry ingredients (the carrageenan and modified starch) are added to the pre-mixed liquid ingredients. The ingredients are mixed together and heated under an applied vacuum to form a molten film-forming composition. In one embodiment, the liquid and dry ingredients are mixed in a double planetary mixer at about 35 RPM for about fifteen minutes. The mixer speed is then reduced to about 20 RPM and a vacuum of 20 inches Hg is applied to the mass for agitation during the melting process. The mass is then further mixed and melted under pressure for about 2.5 hours at a pressure of about 15 inches Hg. The applied pressure acts to eliminate trapped air during the mixing and melting process. The vacuum is released and the additional water, glycerin, and colorants (if any) are added to the mixture. The vacuum is reapplied at 15 inches Hg, and the mass is continually mixed at an elevated temperature for about 1 hour. The mixture is then stored at an elevated temperature. In one embodiment, the mixture is stored at a temperature of about 185 degrees F. The prepared "wet" film-forming composition has a viscosity of less than about 100,000 centa-Poise as measured at 90° C. using a mechanical rheometer at a shear rate of 0 to 100 per second in two (2) minutes, a Brookfield viscometer, or other device known to practitioners in the art to measure viscosity. Preferably, the "wet" film-forming composition has a viscosity less than about 50,000 cP. More preferably, the "wet" film-forming composition has a viscosity less than about 10,000 cP. The "wet" film-forming composition can be used immediately. Alternatively, the "wet" composition can be cooled to room temperature and stored as a gelled mass. The solidified gel mass can be cut into segments, remelted into a molten state, and introduced into the process at a later time.

The prepared molten film-forming composition is then dried to a low water content. For example, the water content may be reduced from at least about 40 percent by weight to less than or equal to about 30 percent by weight. In a particular embodiment, an initial water content of about 57 weight percent is reduced to about 16.5 percent. Reducing the water content to about 16.5 percent by weight yields a dried film-forming composition that can be readily formed into an edible elastic film that can be used to enrobe and encapsulate oral dosage forms using known encapsulation methods. A usable non-gelatin film produced according to a process in accordance with the invention may have a tensile strength at rupture of at least about 0.4 N/mm$^2$ at room temperature. Such a usable film may also have a percent elongation of at least about 50 percent at rupture at room temperature. Continuous agitation and mixing of the film-forming composition during drying may be used to facilitate uniform drying and consistency of the material. The film-forming composition may be heated to between about 210 and about 280 degrees F. under a pressure of about 1-29 inches Hg vacuum during drying.

The dried portion of the film-forming composition is formed into a film. This may be accomplished by passing the dried material through a film-forming device. In one embodiment, the dried portion of the film-forming composition is extruded through a film-forming die to form a film that is about 6 inches wide and about 0.025 inch thick. Films having different widths or thicknesses may be produced in a similar or other suitable manner. The formed film then may be cooled such as by passing the hot film over a chilled setting drum, blowing chilled air over the hot film, or the like. The cooled and set film material then may be passed to an encapsulation or enrobement device for encapsulating or enrobing oral dosage forms.

Figure 2:
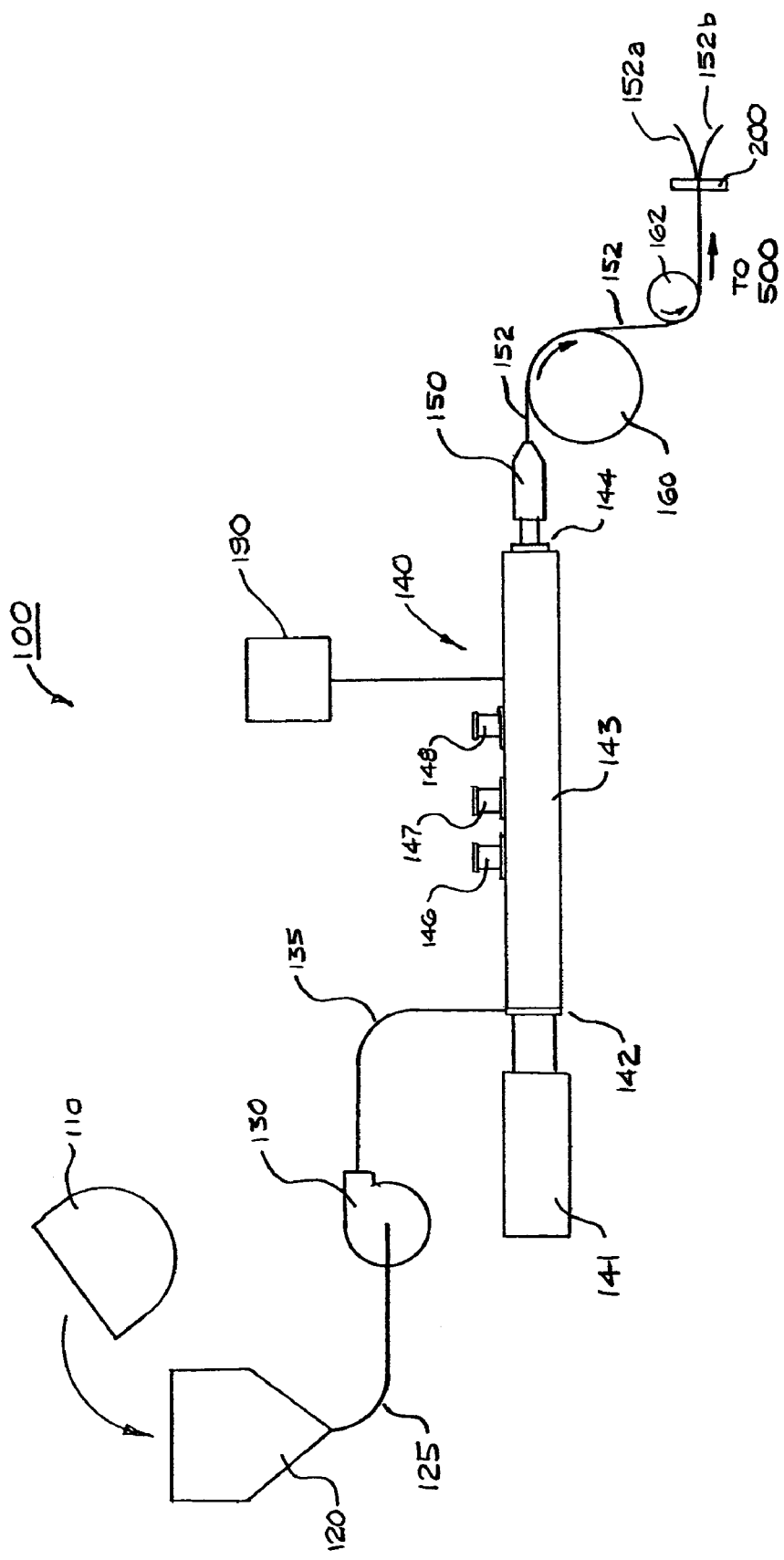
FIG. 2 is a schematic representation of an apparatus for performing the manufacturing process of FIG. 1.

FIG. 2 shows one embodiment of an apparatus 100 that can be used to produce an edible film according to the process described above. In this embodiment, the film-forming composition is substantially fully mixed and heated in a mixer 110. The mixer 110 may be a double planetary mixer such as a Ross Model No. HDM 40. The mixed film-forming composition is then delivered to a heated supply tank 120. The supply tank 120 includes a heating device capable of heating the film-forming composition to a temperature of about 185 degrees F. and maintaining the mass at such temperature.

Conduits 125, 135 connect the supply tank 120 to the inlet end 142 of an extruder/dryer 140. A metering pump 130 can draw portions of the molten film-forming composition from the supply tank 120 through conduit 125 and pump the material at a metered rate to the extruder/dryer 140 through conduit 135. The metering pump 130 may be a Zenith metering gear pump that is capable of delivering the film-forming composition to the extruder/dryer 140 at a metered rate of about 12.5 liters per hour, for example. The extruder/dryer 140 includes a barrel portion 143 and a drive unit 141.

Figure 3:
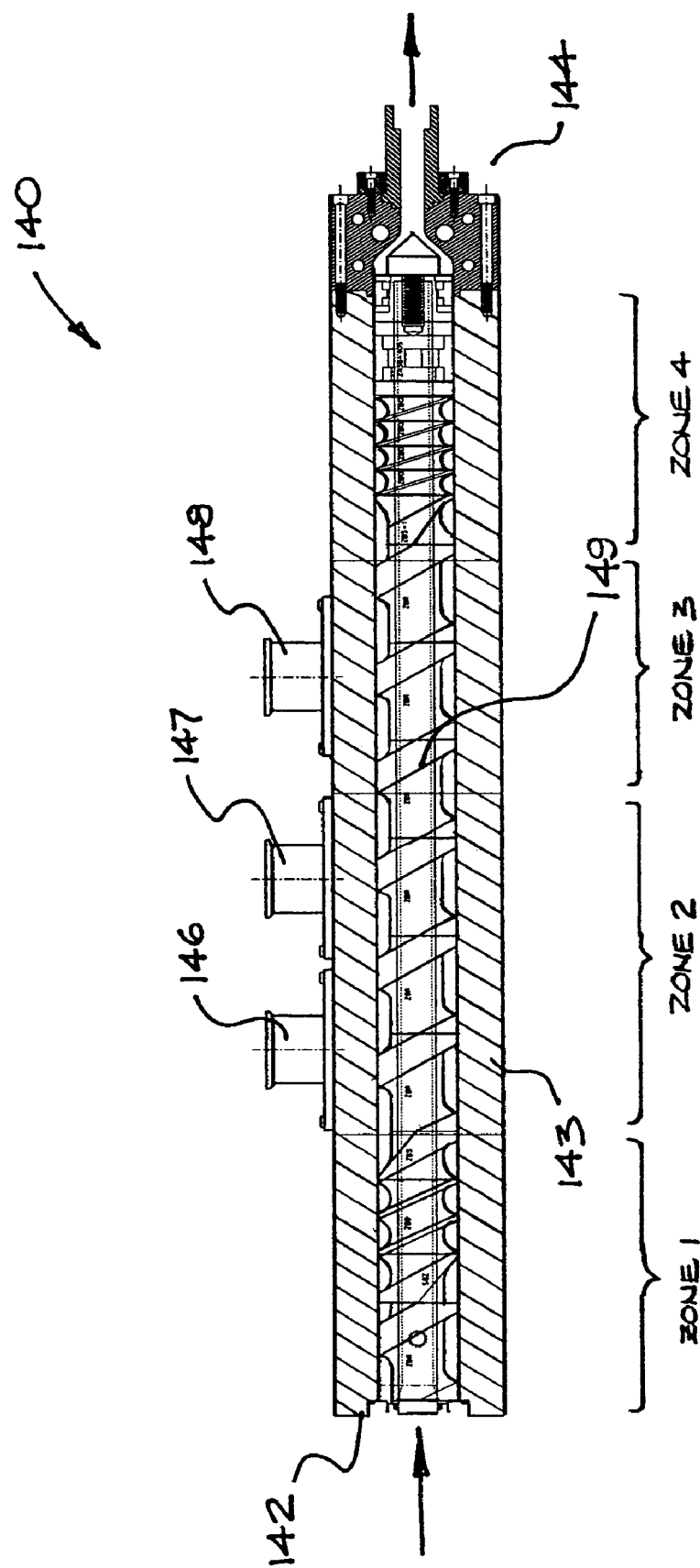
FIG. 3 is a longitudinal cross-sectional view of a extruder/dryer portion of the apparatus of FIG. 2.

In the embodiment shown in FIG. 3, the extruder/dryer 140 includes co-rotating twin screws 149 (one screw is shown) in an elongated barrel 143. The screws 149 of the extruder/dryer 140 are configured such that the film-forming material is urged from the inlet end 142 to the outlet end 144 of the extruder/dryer as the screws 149 are synchronously rotated by the drive unit 141. The screws 149 also are configured to agitate and mix the film-forming material as it passes through the extruder/dryer 140. In one embodiment of the apparatus 100, the screws 149 are about 58 mm in diameter and the screws 149 rotate at about 90 rpm. In this embodiment, the barrel portion of the extruder/dryer 140 is about 1.1 meters in length.

The extruder/dryer 140 may include a series of individually controllable heating zones along its length. One or more heaters in each zone may be controlled by a suitable automatic controller 190 with temperature sensors as required. In one embodiment of the apparatus, the film-forming composition is heated to a temperature of about 270 degrees F. in a first zone (proximate to the inlet end 142), to about 280 degrees F. in a second zone, to about 245 degrees F. in a third zone, and to about 242 degrees in a fourth zone (proximate to the outlet end 144). In this embodiment, the dried film-forming composition exits the extruder/dryer 140 at about 240 degrees F.

As the film-forming composition is heated and agitated in the extruder/dryer 140, water is extracted from the film-forming composition through at least one water extraction port 146, 147, and/or 148. In the embodiment shown in FIGS. 2 and 3, the extruder/dryer 140 includes three water extraction ports 146, 147, 148. Two water extraction ports 146, 147 are provided in zone 2 of the extruder/dryer 140, and a third water extraction port 148 is provided in zone 3 as shown in FIG. 3. More or fewer water extraction ports may be used at various positions along the barrel portion 143 of the extruder/dryer 140. In one embodiment of the apparatus 100, the third water extraction port 148 is capped and is not used. In this embodiment, a vacuum of about 20 inches Hg is applied at the first extraction port 146, and a vacuum of about 21 inches Hg is applied at the second extraction port 147. The vacuum applied at the water extraction ports 146, 147, 148 should be optimized to effectively extract water vapor from the extruder/dryer 140 without also extracting portions of the film-forming composition from the extruder/dryer 140.

Figure 4:
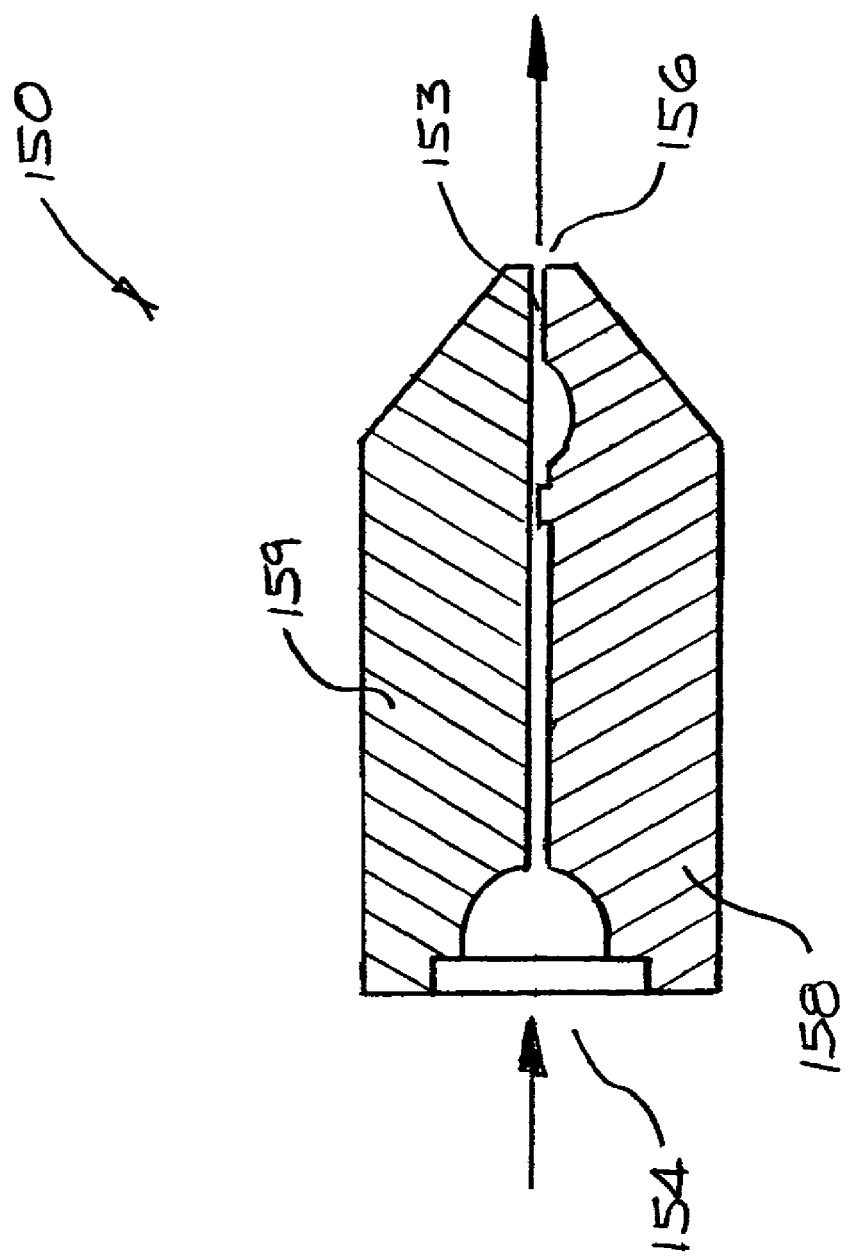
FIG. 4 is a longitudinal cross-sectional view of an extrusion die for use in the apparatus of FIG. 2.

Once the film-forming composition is dried to less than about 25 weight percent water, the film-forming composition is passed from the extruder/dryer 140 to a film-forming device 150, as shown in FIG. 2. In one embodiment, the film-forming device 150 is an extrusion die. A dried portion of the film-forming composition may be supplied directly from the extruder/dryer 140 to an extrusion die 150, as shown in FIG. 4. Alternatively, a dried portion of the film-forming composition may be stored and formed into a film at a later time. In one embodiment, an extrusion die like that shown in FIG. 4 his configured to extrude a ribbon of edible film 152 that is about 6 inches wide and about 0.025 inch thick. The die 150 includes a lower portion 158 and a top portion 159. The film-forming material enters the die 150 through an inlet 154 and exits the die through an outlet 156. The film-forming material is shaped into a ribbon of film as the material is forced through an extrusion channel 153. Other dies that extrude films having different widths and/or thicknesses may also be used. The apparatus 100 may also include a splitting device 200 like that shown in FIG. 2 for splitting the ribbon 152 into two or more separate ribbons of film material. Alternately, a divider at the outlet of the extrusion die may split the film into separate ribbons. In FIG. 4, the ribbon 152 is divided by the splitting device into a first ribbon portion 152a, and a second ribbon portion 152b.

In order to cool and stabilize the extruded film 152, the film 152 may be passed over a chilled setting drum 160 or otherwise cooled as shown in FIG. 2. The film 152 can then be fed directly to an encapsulation or enrobement device 500 for encapsulating or enrobing oral dosage forms in the film 152. For example, the film 152 may be directed to a pair of cooperating rotary dies for encapsulating or enrobing dosage forms in portions of the film 152 (not shown). Encapsulation or enrobement devices like those currently used to encapsulate and/or enrobe oral dosage forms in gelatin-based film materials can be used.

Figure 5:
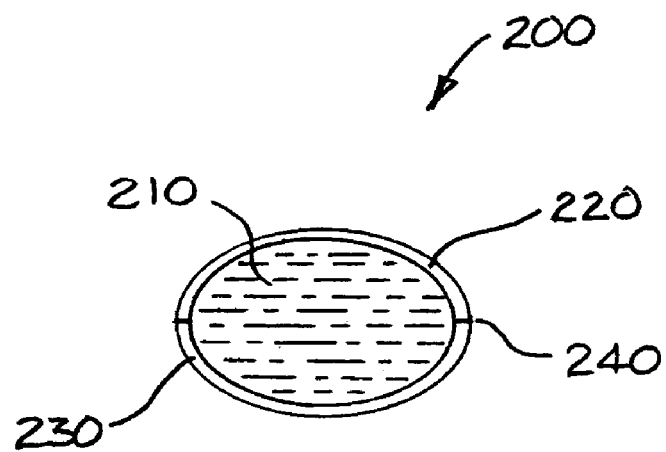
FIG. 5 is a liquid-filled oral dosage form including a shell comprising a film produced according the manufacturing process of in FIG. 1.

FIG. 5 shows an embodiment of a liquid-filled oral dosage form 200 having first and second shell portions 220, 230 formed of an edible non-gelatin film 152 produced by the process and/or apparatus described above. The dosage form 200 includes a liquid fill material 210 encapsulated between a first shell portion 220 and a second shell portion 230. The first and second shell portions 220, 230 are joined at a seam 240 encircling the dosage form 200. The oral dosage form 200 can be produced using known encapsulation methods and equipment such as a rotary die process and apparatus.

Figure 6:
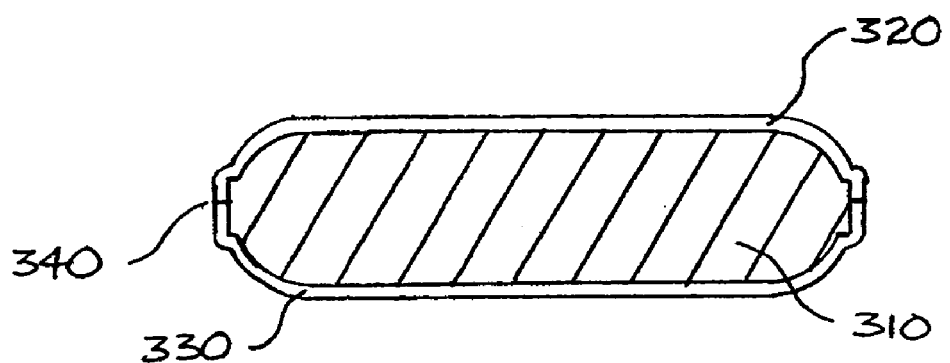
FIG. 6 is an oral dosage form comprising a substantially solid core and a covering comprising a film produced according the manufacturing process of FIG. 1.

An embodiment of a enrobed tablet or caplet 300 having first and second shell portions 320, 330 comprising an edible non-gelatin film 152 produced by the process and/or apparatus described above is shown in FIG. 6. The dosage form 300 includes a substantially solid core 310 enrobed between a first shell portion 320 and a second shell portion 330. The first and second shell portions 320, 330 substantially conform to the outer shape of the core 310, and are sealed together at a seam line 340 encircling the dosage form 300. The oral dosage form 300 can be produced using known enrobement methods and equipment such as a rotary die process and apparatus (not shown).

Once the non-gelatin film 152 has been applied to a dosage form 200 or 300, the film 152 may be further dried to a substantially hard and glassy state. For example, the applied film 152 may be finally dried to a water content of less than about 10 percent by weight by subjecting the applied film 152 to forced dry air.

Although specific embodiments of the present invention have been described in detail, it is to be expressly understood that the invention is not limited thereto. The above detailed description of embodiments of the invention is provided for example only and should not be construed as limiting the invention. Modifications and substitutions will be apparent to those skilled in the art. All such modifications and substitutions are intended to be within the scope of the appended claims.

What is claimed is:

1. A method of producing a non-gelatin film, the method comprising:
   (a) combining at least one non-gelatin hydrocolloid, water, and at least one plasticizer into a substantially homogeneous film-forming composition comprising at least about 40 percent water by weight;
   (b) extracting a portion of the water from the film-forming composition to form a dried portion having a water content of less than or equal to about 25 percent by weight; and
   (c) forming the dried portion of the film-forming composition into a film.

2. A method according to claim 1 wherein combining includes mechanically mixing the hydrocolloid, the water, and the plasticizer.

3. A method according to claim 1 wherein combining includes heating the hydrocolloid, the water, and the plasticizer as they are combined.

4. A method according to claim 1, the method further comprising agitating and heating the film-forming composition as water is extracted.

5. A method according to claim 4 wherein the method further comprises agitating and heating the film-forming composition under pressure.

6. A method according to claim 1 wherein the film-forming composition further comprises a bulking agent.

7. A method according to claim 6 wherein the bulking agent comprises at least one starch ether or at least one esterified starch.

8. A method according to claim 1 wherein the at least one plasticizer is selected from the group consisting of sorbitol, maltitol, and glycerin.

9. A method according to claim 1 wherein the hydrocolloid is selected from the group consisting of carrageenan, alginates, agar, guar, pectin, locust bean gum, xanthan gum, starch, and gellan gum.

10. A method according to claim 1 wherein the hydrocolloid comprises carrageenan.

11. A method according to claim 10 wherein the carrageenan comprises iota carrageenan.

12. A method according to claim 11 wherein the iota carrageenan comprises about 1-15 percent by weight of the film-forming composition.

13. A method according to claim 11 wherein the iota carrageenan comprises about 3-8 percent by weight of the film-forming composition.

14. A method according to claim 10 wherein the carrageenan comprises kappa carrageenan.

15. A method according to claim 14 wherein the kappa carrageenan comprises about 0.5-8 percent by weight of the film-forming composition.

16. A method according to claim 14 wherein the kappa carrageenan comprises about 1-5 percent by weight of the film-forming composition.

17. A method according to claim 1 wherein the film-forming composition comprises:
   (a) about 3-9 weight percent carrageenan;
   (b) about 5-35 weight percent plasticizer; and
   (d) at least about 40 weight percent water.

18. A method according to claim 17 wherein the film-forming composition further comprises about 10-40 weight percent bulking agent.

19. A method according to claim 18 wherein the bulking agent comprises starch.

20. A method according to claim 17 wherein the plasticizer comprises glycerin.

21. A method according to claim 17 wherein the plasticizer comprises sorbitol syrup.

22. A method according to claim 17 wherein the plasticizer comprises maltitol syrup.

23. A method according to claim 1 wherein the film-forming composition comprises:
   (a) about 4-10 weight percent carrageenan;
   (b) about 10-40 weight percent starch;
   (c) about 5-35 weight percent plasticizer; and
   (d) at least about 40 weight percent water.

24. A method according to claim 23 wherein the carrageenan comprises:
   (a) about 1-4 weight percent kappa carrageenan; and
   (b) about 3-8 weight percent iota carrageenan.

25. A method according to claim 1 wherein the dried portion of the film-forming composition comprises about 8-25 percent water by weight.

26. A method according to claim 1 wherein the film-forming composition is preheated to about 180-210 degrees Fahrenheit before water is extracted from the composition.

27. A method according to claim 1 wherein the film-forming composition has a viscosity less than about 100,000 cP as measured at a temperature less than 100 degrees C.

28. A method according to claim 1 wherein the film-forming composition is heated under pressure to a temperature of at least about 210 degrees Fahrenheit as water is extracted from the composition.

29. A method according to claim 28 wherein the pressure is about 1-29 inches Hg.

30. A method according to claim 28 wherein the film-forming composition is heated to a temperature of about 240-280 degrees Fahrenheit as water is extracted from the composition.

31. A method according to claim 1 wherein extracting water from the film-forming composition includes passing the film-forming composition through an extruder/dryer.

32. A method according to claim 31 further comprising agitating the film-forming composition between cooperating rotating twin screws in the extruder/dryer as water is extracted.

33. A method according to claim 1 wherein forming the dried portion of the film-forming composition into a film includes extruding the dried portion through a film-forming die.

34. A method according to claim 1 wherein extracting water from the film-forming composition includes extracting water vapor from the composition by heating the composition and applying a vacuum.

35. A method according to claim 1 wherein the formed film has a tensile strength at rupture of at least about 0.4 Newtons per square millimeter (N/mm$^2$) at room temperature.

36. A method according to claim 1 wherein the formed film has a percent elongation of at least about 50 percent at rupture at room temperature.

37. A method according to claim 1 wherein the film-forming composition has a viscosity of less than about 100,000 cP as measured at a temperature less than about 100 degrees C.

38. A method of producing a non-gelatin film, the method comprising:
(a) combining at least one non-gelatin hydrocolloid, water, and at least one plasticizer into a substantially homogeneous film-forming composition having a water content of at least about 40 percent by weight;
(b) extracting a portion of the water from the film-forming composition to form a dried portion; and
(c) forming the dried portion of the film-forming composition into a film without extracting a substantial additional portion of the water during formation of the film, wherein the formed film has a tensile strength at rupture of at least about 0.4 N/mm$^2$ at room temperature.

39. A method according to claim 38 wherein combining includes mechanically mixing the hydrocolloid, the water, and the plasticizer.

40. A method according to claim 38 wherein combining includes heating the hydrocolloid, the water, and the plasticizer as they are combined.

41. A method according to claim 38, the method further comprising agitating and heating the film-forming composition as water is extracted.

42. A method according to claim 41 wherein the method further comprises agitating and heating the film-forming composition under pressure.

43. A method according to claim 38 wherein the film-forming composition further comprises a bulking agent.

44. A method according to claim 43 wherein the bulking agent comprises at least one starch ether or at least one esterified starch.

45. A method according to claim 38 wherein the at least one plasticizer is selected from the group consisting of sorbitol, maltitol, and glycerin.

46. A method according to claim 38 wherein the hydrocolloid is selected from the group consisting of carrageenan, alginates, agar, guar, pectin, locust bean gum, xanthan gum, starch, and gellan gum.

47. A method according to claim 38 wherein the hydrocolloid comprises carrageenan.

48. A method according to claim 47 wherein the carrageenan comprises iota carrageenan.

49. A method according to claim 48 wherein the iota carrageenan comprises about 1-15 percent by weight of the film-forming composition.

50. A method according to claim 48 wherein the iota carrageenan comprises about 3-8 percent by weight of the film-forming composition.

51. A method according to claim 47 wherein the carrageenan comprises kappa carrageenan.

52. A method according to claim 51 wherein the kappa carrageenan comprises about 0.5-8 percent by weight of the film-forming composition.

53. A method according to claim 51 wherein the kappa carrageenan comprises about 1-5 percent by weight of the film-forming composition.

54. A method according to claim 38 wherein the film-forming composition comprises:
(a) about 3-9 weight percent carrageenan;
(b) about 5-35 weight percent plasticizer; and
(d) at least about 40 weight percent water.

55. A method according to claim 54 wherein the film-forming composition further comprises about 10-40 weight percent bulking agent.

56. A method according to claim 55 wherein the bulking agent comprises starch.

57. A method according to claim 54 wherein the plasticizer comprises glycerin.

58. A method according to claim 54 wherein the plasticizer comprises sorbitol syrup.

59. A method according to claim 54 wherein the plasticizer comprises maltitol syrup.

60. A method according to claim 38 wherein the film-forming composition comprises:
(a) about 4-10 weight percent carrageenan;
(b) about 10-40 weight percent starch;
(c) about 5-35 weight percent plasticizer; and
(d) at least about 40 weight percent water.

61. A method according to claim 60 wherein the carrageenan comprises:
(a) about 1-2 weight percent kappa carrageenan; and
(b) about 3-5 weight percent iota carrageenan.

62. A method according to claim 38 wherein the dried portion of the film-forming composition comprises about 8-25 percent water by weight.

63. A method according to claim 38 wherein the film-forming composition is preheated to about 180-210 degrees Fahrenheit before water is extracted from the composition.

64. A method according to claim 38 wherein the film-forming composition has a viscosity less than about 100,000 cP as measured at a temperature less than 100 degrees C.

65. A method according to claim 38 wherein the film-forming composition is heated under pressure to a temperature of at least about 240 degrees as water is extracted from the composition.

66. A method according to claim 65 wherein the pressure is about 1-29 inches Hg.

67. A method according to claim 65 wherein the film-forming composition is heated to a temperature of about 240-280 degrees Fahrenheit as water is extracted from the composition.

68. A method according to claim 38 wherein extracting water from the film-forming composition includes passing the film-forming composition through an extruder/dryer.

69. A method according to claim 68 further comprising agitating the film-forming composition between cooperating rotating twin screws in the extruder/dryer as water is extracted.

70. A method according to claim 38 wherein forming the dried portion of the film-forming composition into a film includes extruding the dried portion through a film-forming die.

71. A method according to claim 38 wherein extracting water from the film-forming composition includes extracting water vapor from the composition by heating the composition and applying a vacuum.

72. A method according to claim 38 wherein the dried portion of the film-forming composition has a water content of less than or equal to about 25 percent by weight.

73. A method according to claim 38 wherein the formed film has a percent elongation of at least about 50 percent at rupture at room temperature.

74. A method according to claim 38 wherein the film-forming composition has a viscosity of less than about 100,000 cP as measured at a temperature less than about 100 degrees C.

75. A method of producing a non-gelatin film, the method comprising:
(a) combining at least one non-gelatin hydrocolloid, water, and at least one plasticizer into a substantially homogeneous film-forming composition comprising at least about 40 percent water by weight;
(b) extracting a portion of the water from the film-forming composition to form a dried portion;

(c) forming the dried portion of the film-forming composition into a film without extracting a substantial additional portion of the water while forming the film, the formed film having a percent elongation of at least about 50 percent at rupture at room temperature.

76. A method according to claim 75 wherein combining includes mechanically mixing the hydrocolloid, the water, and the plasticizer.

77. A method according to claim 75 wherein combining includes heating the hydrocolloid, the water, and the plasticizer as they are combined.

78. A method according to claim 75, the method further comprising agitating and heating the film-forming composition as water is extracted.

79. A method according to claim 78 wherein the method further comprises agitating and heating the film-forming composition under pressure.

80. A method according to claim 75 wherein the film-forming composition further comprises a bulking agent.

81. A method according to claim 80 wherein the bulking agent comprises at least one starch ether or at least one esterified starch.

82. A method according to claim 75 wherein the at least one plasticizer is selected from the group consisting of sorbitol, maltitol, and glycerin.

83. A method according to claim 75 wherein the hydrocolloid is selected from the group consisting of carrageenan, alginates, agar, guar, pectin, locust bean gum, xanthan gum, starch, and gellan gum.

84. A method according to claim 75 wherein the hydrocolloid comprises carrageenan.

85. A method according to claim 84 wherein the carrageenan comprises iota carrageenan.

86. A method according to claim 85 wherein the iota carrageenan comprises about 1-15 percent by weight of the film-forming composition.

87. A method according to claim 85 wherein the iota carrageenan comprises about 3-8 percent by weight of the film-forming composition.

88. A method according to claim 84 wherein the carrageenan comprises kappa carrageenan.

89. A method according to claim 88 wherein the kappa carrageenan comprises about 0.5-8 percent by weight of the film-forming composition.

90. A method according to claim 88 wherein the kappa carrageenan comprises about 1-5 percent by weight of the film-forming composition.

91. A method according to claim 75 wherein the film-forming composition comprises:
(a) about 3-9 weight percent carrageenan;
(b) about 5-35 weight percent plasticizer; and
(d) at least about 40 weight percent water.

92. A method according to claim 91 wherein the film-forming composition further comprises about 10-40 weight percent bulking agent.

93. A method according to claim 92 wherein the bulking agent comprises starch.

94. A method according to claim 91 wherein the plasticizer comprises glycerin.

95. A method according to claim 91 wherein the plasticizer comprises sorbitol syrup.

96. A method according to claim 91 wherein the plasticizer comprises maltitol syrup.

97. A method according to claim 75 wherein the film-forming composition comprises:
(a) about 4-10 weight percent carrageenan;
(b) about 10-40 weight percent starch;
(c) about 5-35 weight percent plasticizer; and
(d) at least about 40 weight percent water.

98. A method according to claim 97 wherein the carrageenan comprises:
(a) about 1-2 weight percent kappa carrageenan; and
(b) about 3-5 weight percent iota carrageenan.

99. A method according to claim 75 wherein the dried portion of the film-forming composition comprises about 8-25 percent water by weight.

100. A method according to claim 75 wherein the film-forming composition is preheated to about 180-210 degrees Fahrenheit before water is extracted from the composition.

101. A method according to claim 75 wherein the film-forming composition has a viscosity less than about 100,000 cP as measured at a temperature less than 100 degrees C.

102. A method according to claim 75 wherein the film-forming composition is heated under pressure to a temperature of at least about 240 degrees as water is extracted from the composition.

103. A method according to claim 102 wherein the pressure is about 1-29 inches Hg.

104. A method according to claim 102 wherein the film-forming composition is heated to a temperature of about 240-280 degrees Fahrenheit as water is extracted from the composition.

105. A method according to claim 75 wherein extracting water from the film-forming composition includes passing the film-forming composition through an extruder/dryer.

106. A method according to claim 105 further comprising agitating the film-forming composition between cooperating rotating twin screws in the extruder/dryer as water is extracted.

107. A method according to claim 75 wherein forming the dried portion of the film-forming composition into a film includes extruding the dried portion through a film-forming die.

108. A method according to claim 75 wherein extracting water from the film-forming composition includes extracting water vapor from the composition by heating the composition and applying a vacuum.

109. A method according to claim 75 wherein the formed film has a tensile strength at rupture of at least about 0.4 N/mm$^2$ at room temperature.

110. A method according to claim 75 wherein the dried portion of the film-forming composition has a water content less than or equal to about 25 percent by weight.

111. A method according to claim 75 wherein the film-forming composition has a viscosity of less than about 100,000 cP as measured at a temperature less than about 100 degrees C.

112. A method of producing a non-gelatin film, the method comprising:
(a) combining at least one non-gelatin hydrocolloid, water, and at least one plasticizer into a substantially homogeneous film-forming composition having a viscosity of less than about 100,000 cP as measured at a temperature less than about 100 degrees C.;
(b) extracting a portion of the water from the film-forming composition to form a dried portion having a water content less than or equal to about 25 percent by weight; and
(c) forming the dried portion of the film-forming composition into a film.

113. A method according to claim 112 wherein combining includes mechanically mixing the hydrocolloid, the water, and the plasticizer.

114. A method according to claim 112 wherein combining includes heating the hydrocolloid, the water, and the plasticizer as they are combined.

115. A method according to claim 112, the method further comprising agitating and heating the film-forming composition as water is extracted.

116. A method according to claim 115 wherein the method further comprises agitating and heating the film-forming composition under pressure.

117. A method according to claim 112 wherein the film-forming composition further comprises a bulking agent.

118. A method according to claim 117 wherein the bulking agent comprises at least one starch ether or at least one esterified starch.

119. A method according to claim 112 wherein the at least one plasticizer is selected from the group consisting of sorbitol, maltitol, and glycerin.

120. A method according to claim 112 wherein the hydrocolloid is selected from the group consisting of carrageenan, alginates, agar, guar, pectin, locust bean gum, xanthan gum, starch, and gellan gum.

121. A method according to claim 112 wherein the hydrocolloid comprises carrageenan.

122. A method according to claim 121 wherein the carrageenan comprises iota carrageenan.

123. A method according to claim 122 wherein the iota carrageenan comprises about 1-15 percent by weight of the film-forming composition.

124. A method according to claim 122 wherein the iota carrageenan comprises about 3-8 percent by weight of the film-forming composition.

125. A method according to claim 121 wherein the carrageenan comprises kappa carrageenan.

126. A method according to claim 125 wherein the kappa carrageenan comprises about 0.5-8 percent by weight of the film-forming composition.

127. A method according to claim 125 wherein the kappa carrageenan comprises about 1-5 percent by weight of the film-forming composition.

128. A method according to claim 112 wherein the film-forming composition comprises:
    (a) about 3-9 weight percent carrageenan;
    (b) about 5-35 weight percent plasticizer; and
    (d) at least about 40 weight percent water.

129. A method according to claim 128 wherein the film-forming composition further comprises about 10-40 weight percent bulking agent.

130. A method according to claim 129 wherein the bulking agent comprises starch.

131. A method according to claim 128 wherein the plasticizer comprises glycerin.

132. A method according to claim 128 wherein the plasticizer comprises sorbitol syrup.

133. A method according to claim 128 wherein plasticizer comprises maltitol syrup.

134. A method according to claim 112 wherein the film-forming composition comprises:
    (a) about 4-10 weight percent carrageenan;
    (b) about 10-40 weight percent starch;
    (c) about 5-35 weight percent plasticizer; and
    (d) at least about 40 weight percent water.

135. A method according to claim 134 wherein the carrageenan comprises:
    (a) about 1-2 weight percent kappa carrageenan; and
    (b) about 3-5 weight percent iota carrageenan.

136. A method according to claim 112 wherein the dried portion of the film-forming composition comprises about 8-25 percent water by weight.

137. A method according to claim 112 wherein the film-forming composition is preheated to about 180-210 degrees Fahrenheit before water is extracted from the composition.

138. A method according to claim 112 wherein the film-forming composition has a viscosity less than about 100,000 cP as measured at a temperature less than 100 degrees C.

139. A method according to claim 112 wherein the film-forming composition is heated under pressure to a temperature of at least about 240 degrees as water is extracted from the composition.

140. A method according to claim 139 wherein the pressure is about 1-29 inches Hg.

141. A method according to claim 139 wherein the film-forming composition is heated to a temperature of about 240-280 degrees Fahrenheit as water is extracted from the composition.

142. A method according to claim 112 wherein extracting water from the film-forming composition includes passing the film-forming composition through an extruder/dryer.

143. A method according to claim 142 further comprising agitating the film-forming composition between cooperating rotating twin screws in the extruder/dryer as water is extracted.

144. A method according to claim 112 wherein forming the dried portion of the film-forming composition into a film includes extruding the dried portion through a film-forming die.

145. A method according to claim 112 wherein extracting water from the film-forming composition includes extracting water vapor from the composition by heating the composition and applying a vacuum.

146. A method according to claim 112 wherein the formed film has a tensile strength at rupture of at least about 0.4 N/mm$^2$ at room temperature.

147. A method according to claim 112 wherein the formed film has a percent elongation of at least about 50 percent at rupture at room temperature.

148. A method of producing a non-gelatin film, the method comprising:
    (a) combining at least one non-gelatin hydrocolloid, water, and at least one plasticizer into a substantially homogeneous film-forming composition having a viscosity of less than about 100,000 cP as measured at a temperature less than about 100 degrees C.;
    (b) extracting a portion of the water from the film-forming composition to form a dried portion; and
    (c) forming the dried portion of the film-forming composition into a film without extracting a substantial additional portion of the water while forming the film, wherein the formed film has a tensile strength at rupture of at least about 0.4 N/mm$^2$ at room temperature.

149. A method according to claim 148 wherein combining includes mechanically mixing the hydrocolloid, the water, and the plasticizer.

150. A method according to claim 148 wherein combining includes heating the hydrocolloid, the water, and the plasticizer as they are combined.

151. A method according to claim 148, the method further comprising agitating and heating the film-forming composition as water is extracted.

152. A method according to claim 148 wherein the method further comprises agitating and heating the film-forming composition under pressure.

153. A method according to claim 148 wherein the film-forming composition further comprises a bulking agent.

154. A method according to claim 153 wherein the bulking agent comprises at least one starch ether or at least one esterified starch.

155. A method according to claim 148 wherein the at least one plasticizer is selected from the group consisting of sorbitol, maltitol, and glycerin.

156. A method according to claim 148 wherein the hydrocolloid is selected from the group consisting of carrageenan, alginates, agar, guar, pectin, locust bean gum, xanthan gum, starch, and gellan gum.

157. A method according to claim 148 wherein the hydrocolloid comprises carrageenan.

158. A method according to claim 157 wherein the carrageenan comprises iota carrageenan.

159. A method according to claim 158 wherein the iota carrageenan comprises about 1-15 percent by weight of the film-forming composition.

160. A method according to claim 158 wherein the iota carrageenan comprises about 3-8 percent by weight of the film-forming composition.

161. A method according to claim 157 wherein the carrageenan comprises kappa carrageenan.

162. A method according to claim 161 wherein the kappa carrageenan comprises about 0.5-8 percent by weight of the film-forming composition.

163. A method according to claim 161 wherein the kappa carrageenan comprises about 1-5 percent by weight of the film-forming composition.

164. A method according to claim 148 wherein the film-forming composition comprises:
 (a) about 3-9 weight percent carrageenan;
 (b) about 5-35 weight percent plasticizer; and
 (d) at least about 40 weight percent water.

165. A method according to claim 164 wherein the film-forming composition further comprises about 10-40 weight percent bulking agent.

166. A method according to claim 165 wherein the bulking agent comprises starch.

167. A method according to claim 164 wherein the plasticizer further comprises glycerin.

168. A method according to claim 164 wherein the plasticizer comprises sorbitol syrup.

169. A method according to claim 164 wherein the plasticizer comprises maltitol syrup.

170. A method according to claim 148 wherein the film-forming composition comprises:
 (a) about 4-10 weight percent carrageenan;
 (b) about 10-40 weight percent starch;
 (c) about 5-35 weight percent plasticizer; and
 (d) at least about 40 weight percent water.

171. A method according to claim 170 wherein the carrageenan comprises:
 (a) about 1-2 weight percent kappa carrageenan; and
 (b) about 3-5 weight percent iota carrageenan.

172. A method according to claim 148 wherein the dried portion of the film-forming composition comprises about 8-25 percent water by weight.

173. A method according to claim 148 wherein the film-forming composition is preheated to about 180-210 degrees Fahrenheit before water is extracted from the composition.

174. A method according to claim 148 wherein the film-forming composition has a viscosity less than about 100,000 cP as measured at a temperature less than 100 degrees C.

175. A method according to claim 148 wherein the film-forming composition is heated under pressure to a temperature of at least about 240 degrees as water is extracted from the composition.

176. A method according to claim 175 wherein the pressure is about 1-29 inches Hg.

177. A method according to claim 175 wherein the film-forming composition is heated to a temperature of about 240-280 degrees Fahrenheit as water is extracted from the composition.

178. A method according to claim 148 wherein extracting water from the film-forming composition includes passing the film-forming composition through an extruder/dryer.

179. A method according to claim 178 further comprising agitating the film-forming composition between cooperating rotating twin screws in the extruder/dryer as water is extracted.

180. A method according to claim 148 wherein forming the dried portion of the film-forming composition into a film includes extruding the dried portion through a film-forming die.

181. A method according to claim 148 wherein extracting water from the film-forming composition includes extracting water vapor from the composition by heating the composition and applying a vacuum.

182. A method according to claim 148 wherein the film-forming material has a water content of at least about 40 percent by weight.

183. A method according to claim 148 wherein the formed film has a percent elongation of at least about 50 percent at rupture at room temperature.

184. A method according to claim 148 wherein the dried portion of the film-forming composition has a water content of less than or equal to about 25 percent by weight.

185. A method of producing a non-gelatin film, the method comprising:
 (a) combining at least one non-gelatin hydrocolloid, water, and at least one plasticizer into a substantially homogeneous film-forming composition having a viscosity of less than about 100,000 cP as measured at a temperature less than about 100 degrees C.;
 (b) extracting a portion of the water from the film-forming composition to form a dried portion; and
 (c) forming the dried portion of the film-forming composition into a film without extracting a substantial additional portion of the water while forming the film, the formed film having a percent elongation of at least about 50 percent at rupture at room temperature.

186. A method according to claim 185 wherein combining includes mechanically mixing the hydrocolloid, the water, and the plasticizer.

187. A method according to claim 185 wherein combining includes heating the hydrocolloid, the water, and the plasticizer as they are combined.

188. A method according to claim 185, the method further comprising agitating and heating the film-forming composition as water is extracted.

189. A method according to claim 188 wherein the method further comprises agitating and heating the film-forming composition under pressure.

190. A method according to claim 185 wherein the film-forming composition further comprises a bulking agent.

191. A method according to claim 190 wherein the bulking agent comprises at least one starch ether or at least one esterified starch.

192. A method according to claim 185 wherein the at least one plasticizer is selected from the group consisting of sorbitol, maltitol, and glycerin.

193. A method according to claim 185 wherein the hydrocolloid is selected from the group consisting of carrageenan, alginates, agar, guar, pectin, locust bean gum, xanthan gum, starch, and gellan gum.

194. A method according to claim 185 wherein the hydrocolloid comprises carrageenan.

195. A method according to claim 194 wherein the carrageenan comprises iota carrageenan.

196. A method according to claim 195 wherein the iota carrageenan comprises about 1-15 percent by weight of the film-forming composition.

197. A method according to claim 195 wherein the iota carrageenan comprises about 3-8 percent by weight of the film-forming composition.

198. A method according to claim 194 wherein the carrageenan comprises kappa carrageenan.

199. A method according to claim 198 wherein the kappa carrageenan comprises about 0.5-8 percent by weight of the film-forming composition.

200. A method according to claim 198 wherein the kappa carrageenan comprises about 1-5 percent by weight of the film-forming composition.

201. A method according to claim 185 wherein the film-forming composition comprises:
(a) about 3-9 weight percent carrageenan;
(b) about 5-35 weight percent plasticizer; and
(d) at least about 40 weight percent water.

202. A method according to claim 201 wherein the film-forming composition further comprises about 10-40 weight percent bulking agent.

203. A method according to claim 202 wherein the bulking agent comprises starch.

204. A method according to claim 201 wherein the plasticizer comprises glycerin.

205. A method according to claim 196 wherein the plasticizer comprises sorbitol syrup.

206. A method according to claim 196 wherein the plasticizer comprises maltitol syrup.

207. A method according to claim 185 wherein the film-forming composition comprises:
(a) about 4-10 weight percent carrageenan;
(b) about 10-40 weight percent starch;
(c) about 5-35 weight percent plasticizer; and
(d) at least about 40 weight percent water.

208. A method according to claim 201 wherein the carrageenan comprises:
(a) about 1-2 weight percent kappa carrageenan; and
(b) about 3-5 weight percent iota carrageenan.

209. A method according to claim 185 wherein the dried portion of the film-forming composition comprises about 8-25 percent water by weight.

210. A method according to claim 185 wherein the film-forming composition is preheated to about 180-210 degrees Fahrenheit before water is extracted from the composition.

211. A method according to claim 185 wherein the film-forming composition has a viscosity less than about 100,000 cP as measured at a temperature less than 100 degrees C.

212. A method according to claim 185 wherein the film-forming composition is heated under pressure to a temperature of at least about 240 degrees as water is extracted from the composition.

213. A method according to claim 212 wherein the pressure is about 1-29 inches Hg.

214. A method according to claim 212 wherein the film-forming composition is heated to a temperature of about 240-280 degrees Fahrenheit as water is extracted from the composition.

215. A method according to claim 185 wherein extracting water from the film-forming composition includes passing the film-forming composition through an extruder/dryer.

216. A method according to claim 215 further comprising agitating the film-forming composition between cooperating rotating twin screws in the extruder/dryer as water is extracted.

217. A method according to claim 185 wherein forming the dried portion of the film-forming composition into a film includes extruding the dried portion through a film-forming die.

218. A method according to claim 185 wherein extracting water from the film-forming composition includes extracting water vapor from the composition by heating the composition and applying a vacuum.

219. A method according to claim 185 wherein the formed film has a tensile strength at rupture of at least about 0.4 $N/mm^2$ at room temperature.

220. A method according to claim 185 wherein the film-forming composition comprises at least about 40 percent water by weight.

221. A method according to claim 185 wherein the dried portion of the film-forming composition has a water content less than or equal to about 25 percent by weight.

222. A method of producing a non-gelatin film, the method comprising:
(a) combining at least one non-gelatin hydrocolloid, water, and at least one plasticizer into a substantially homogeneous film-forming composition comprising at least about 40 percent water by weight;
(b) extracting a portion of the water from the film-forming composition to form a dried portion having a water content of less than or equal to about 25 percent by weight; and
(c) forming the dried portion of the film-forming composition into a film without extracting a substantial additional portion of the water while forming the film.

223. A method of producing a non-gelatin film, the method comprising:
(a) combining at least one non-gelatin hydrocolloid, water, and at least one plasticizer into a substantially homogeneous film-forming composition having a viscosity of less than about 100,000 cP as measured at a temperature less than about 100 degrees C.;
(b) extracting a portion of the water from the film-forming composition to form a dried portion having a water content less than or equal to about 25 percent by weight; and
(c) forming the dried portion of the film-forming composition into a film without extracting a substantial additional portion of the water while forming the film.

* * * * *